(12) United States Patent
Agrofoglio et al.

(10) Patent No.: US 8,785,629 B2
(45) Date of Patent: Jul. 22, 2014

(54) PHOSPHONATES SYNTHONS FOR THE SYNTHESIS OF PHOSPHONATES DERIVATIVES SHOWING BETTER BIOAVAILABILITY

(75) Inventors: Luigi A. Agrofoglio, Orleans (FR); Vincent Roy, Pussay (FR); Ugo Pradere, Lusignan (FR)

(73) Assignees: Centre National de la Recherche Scientifique, Paris (FR); Universite d'Orleans, Orleans (FR)

( * ) Notice: Subject to any disclaimer, the term of this patent is extended or adjusted under 35 U.S.C. 154(b) by 39 days.

(21) Appl. No.: 13/377,652

(22) PCT Filed: Jun. 17, 2010

(86) PCT No.: PCT/EP2010/058567
§ 371 (c)(1),
(2), (4) Date: Feb. 24, 2012

(87) PCT Pub. No.: WO2010/146127
PCT Pub. Date: Dec. 23, 2010

(65) Prior Publication Data
US 2012/0142897 A1    Jun. 7, 2012

(30) Foreign Application Priority Data

Jun. 18, 2009  (EP) .................................... 09305562

(51) Int. Cl.
*C07F 9/06* (2006.01)
*C07F 9/40* (2006.01)

(52) U.S. Cl.
USPC ........... 544/232; 549/219; 558/156; 558/180; 558/183

(58) Field of Classification Search
USPC ........... 530/352; 544/232; 549/219; 558/156, 558/180, 183
See application file for complete search history.

(56) References Cited

FOREIGN PATENT DOCUMENTS

| DE | 1805677 A1 | 12/1969 |
|---|---|---|
| DE | 2002807 A1 | 7/1970 |
| GB | 1239988 A | 7/1971 |

OTHER PUBLICATIONS

Somogyi Gabor et al: "Targeted drug delivery to the brain via phosphonate derivatives", International Journal of Pharmaceutics 166 (1988), Nov. 11, 1998, pp. 15-26, XP002555028.

Gong-Xin He et al: "Chapter 3.6. Prodrugs of Phosphonates, Phosphinates, and Phosphates" Prodrugs Challenges and Rewards Part 1 (Book Series: Biotechnology: Pharmaceutical Aspects), Springer New York, US, vol. 5, Jan. 1, 2007, pp. 923-964, XP001539680.

International Search Report, dated Jul. 19, 2010, in PCT/EP2010/058567.

*Primary Examiner* — Kristin Vajda
(74) *Attorney, Agent, or Firm* — Young & Thompson

(57) ABSTRACT

Synthons for the synthesis of phosphonates prodrugs POM and POC, especially for direct Cross Metathesis.

5 Claims, 1 Drawing Sheet

|  | *c* Log D (pH = 7.4) | | | | |
|---|---|---|---|---|---|
| Molecules | R = R' = H | R = R' = POM | R = R' = POC | R = POC ; R' = HDP | R = H ; R' = HDP |
| (uracil deriv.) | -3.53 | 3.43 | 2.61 | 7.53 | 3.34 |
| (5-F uracil deriv.) | -3.37 | 3.58 | 2.77 | 7.69 | 3.49 |
| (5-Cl uracil deriv.) | -2.91 | 4.04 | 3.23 | 8.25 | 3.95 |
| (5-Br uracil deriv.) | -2.70 | 4.26 | 3.44 | 8.36 | 4.17 |
| (5-I uracil deriv.) | -2.58 | 4.37 | 3.56 | 8.48 | 4.28 |
| (5-Me uracil deriv.) | -3.18 | 3.78 | 2.96 | 7.88 | 3.69 |
| (adenine deriv.) | -3.49 | 3.46 | | | |
| (6-Cl purine deriv.) | -2.48 | 4.48 | | | |
| (6-Cl, 2-NH₂ purine deriv.) | -2.59 | 4.36 | | | |
| (hypoxanthine deriv.) | -4.21 | 2.74 | | | |
| (guanine deriv.) | -4.30 | 2.65 | | | |
| (6-cyclopropylamino purine deriv.) | -2.72 | 4.24 | | | |
| (6-cyclopropylamino, 2-NH₂ purine deriv.) | -2.85 | 4.10 | | | |
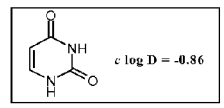
*c* log D = -0.86
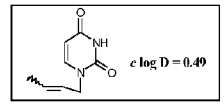
*c* log D = 0.49

PHOSPHONATES SYNTHONS FOR THE SYNTHESIS OF PHOSPHONATES DERIVATIVES SHOWING BETTER BIOAVAILABILITY

Provided herein are synthons useful for the synthesis of phosphonates compounds or derivatives showing better bioavailability, processes for their preparation and their use in the synthesis of phosphonates compounds or derivatives showing better bioavailability.

Several biologically active molecules are bearing a phosphonate moiety. As for instance, certain aryl-substituted ketophosphonates have been reported to have bone anabolic activity (see, e.g., WO 2004/026245) or to function as thyroid receptor ligands (see, e.g., US 2006/0046980), meanwhile bisphosphonic acids (also known as diphosphonic acids) and their salts are a class of compounds that are cytotoxic to osteoclasts and act to prevent bone resorption; when conjugated with alkylating moieties, bis-phosphonates have been reported to have antitumor activity (see, e.g., WO 9843987). The pyrazolopyrimidine and pyrimidinyl bisphosphonic esters are anti-inflammatory agents (see, e.g., U.S. Pat. No. 5,397,774), meanwhile macrocyclic phosphonates and amidophosphates have been reported to inhibit HCV (see, e.g., WO 2008096002); several phosphonate analogs of HIV protease inhibitors have an improved cellular accumulation properties (see, e.g., WO 2003090690); some heteroaromatic phosphonates were tested for a variety of biological activities including inhibition of fructose 1,6-bisphosphatase (FBPase) and activity toward AMP binding enzymes, such as adenosine kinase, and are useful in the treatment of diabetes and other diseases where inhibition of gluconeogenesis, control of blood glucose levels, reduction in glycogen storage, or reduction in insulin levels is beneficial (see, e.g., US 1998-135504P); dihydropyridine-5-phosphonate derivatives are effective Ca antagonists (see, e.g., JP 60069089); some pyrimidyl phosphonates act as brain performance disturbance and depression treatment agents (see, e.g., DE 1993-4343599); some phosphonates with alkenes derivatives are known as antibacterial (DE 18 05 677 A1) and antibiotics (DE 20 02 807); Other compounds, such as nucleoside derivatives or analogs, are active agents that are administered in non-phosphorylated form, but are phosphorylated in vivo in the form of metabolic monophosphate or triphosphate to become active. Thus, nucleoside derivatives having antitumor activity, such as 5-fluorouridine, 5-fluoro-2'-deoxyuridine or antiviral activity (in the treatment of AIDS, hepatitis B or C), such as 2',3'-dideoxynucleosides, acyclonucleoside phosphonates, exert their activity in phosphorylated form as phosphate or phosphonates analogs.

Compounds bearing a phosphonate group have a negatively charged ionic nature at physiological pH. The therapeutic activity of such compounds is consequently limited, on account of the low diffusion of negatively charged compounds across biological lipid membranes. In particular, charged compounds do not diffuse efficiently across cell membranes, or indeed across the cerebral barrier, which are lipidic in nature. Thus, one solution to drug delivery and/or bioavailability issues in pharmaceutical development is converting known phosphonate drugs to phosphonate prodrugs. Typically, in a phosphonate prodrug, the polar functional group is masked by a pro-moiety, which is labile under physiological conditions. Accordingly, prodrugs are usually transported through hydrophobic biological barriers such as membranes and typically possess superior physicochemical properties in comparison to the parent drug. For instance, in the nucleoside domain, numerous studies showed the importance of having monophosphates or phosphonates of said nucleosides in order to present a better bioavailability (pro-nucleosides). Several compounds without any biological activity became also active when converted to monophosphate or phosphonate derivatives (Somogyi Gabor et al. <<Targeted drug delivery to the brain via phosphonates derivatives>>, IJP 166, 2008, p. 15-26 and Gong-Xin et al: <<Chapter 3.6. Prodrugs of Phosphonates, Phosphinates and Phosphates>>, Prodrugs Challenges and Reward Part 1. Springer New York, US, vol. 5.1, 2007, p. 923-964).

Generally, most of the methods, which are use for introducing a biolabile moiety onto a phosphonate group, comprise several steps (e.g., deprotection of a dimethyl, diethyl or diisopropyl phosphonate under harsh conditions, its activation and its substitution by a biolabile group), poor yields, purification on reverse phase column and structural restrictions to the use of the synthons.

Thus, the present invention satisfies these and other needs by providing synthons useful for the synthesis of phosphonates derivatives showing better bioavailability, processes for their preparation and their use in the synthesis of phosphonates derivatives showing better bioavailability. The inventors discovered new processes for synthesizing phosphonate synthons bearing a biolabile moiety which can be used to (a) either transform a said compound into its phosphonate analogue, (2) to synthesize a phosphonate compound. They prepared several phosphonates derivatives which bear independently of each other either (a) an ester function or analoguous, said function being optionally bio-labile, and/or lipidic chain, (b) an unsaturated (alkene, alyne, allene) function or analogous (c) a nucleofuge or (d) a hydrogen atom or (e) a methyl group directly linked to a phosphate group. Use of such derivatives in (a) olefin cross metathesis route, (b) nucleophilic substitution reaction (c) dipolar [1,3]-cycloaddition, (d) amination, (e) ring-opening, (f) addition of carbonyl and analogues, (g) organometallic cross-coupling, especially catalyzed by Pd(0), for instance, permit to convert a compound into its phosphonate diester, unsymmetrical diester, or monoester said phosphonate presenting a better bioavailability. The synthons according to the invention show several advantages: convergent synthesis on high scale, easy purification, and easy transformation of product with a better bioavailability.

Thus an object of the instant invention is a compound of formula (I)

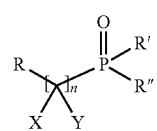

(I)

wherein
R represents
a group of formula (1)

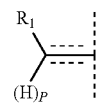

(1)

wherein $R_1$ represents H, a straight or branched ($C_1$-$C_6$) alkyl group or a —$(CH_2)_m$—$R_2$ group with $R_2$ selected from the group comprising Hydrogen, halogen, OH, $N_3$, $NH_2$, epoxy groups, leaving groups and carbonyl groups and m is an integer from 0 to 5,
===== represents a double or a triple bond,
p being equal to 0 when ===== is a triple bond and equal to 1 when
===== is a double bond or,
$R=R_2$ with $R_2$ selected from the group comprising hydrogen, halogen, OH, $N_3$, $NH_2$, epoxy groups and analogs, leaving groups (sulfonates, halogens, . . . ), leaving groups involved into a transmetalation step catalyzed by Pd(0), and carbonyl groups,
n is an integer from 0 to 5
X and Y independently of each other represent hydrogen, halogen, a straight or branched $(C_1$-$C_6)$alkyl group or an hydroxymethyl group, and
R' and R" independently of each other
represent a group selected from the group comprising an oxymethylcarbonyl group of formula (2)

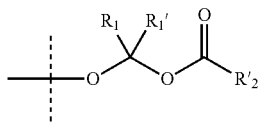

(2)

wherein
$R_1$ and $R'_1$ are independently of each other hydrogen or $(C_1$-$C_4)$alkyl group and
$R'_2$ is a straight or branched $(C_1$-$C_6)$alkyl group or straight or branched $(C_1$-$C_6)$alkoxy group
with the proviso that when R is cis-propenyl

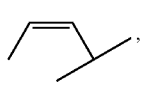

n=0 and R'2 is methyl, then R1 and R' 1 are not simultaneously hydrogen,
a thioethylcarbonyl group of formula (3)

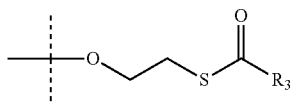

(3)

wherein
$R_3$ is a straight or branched $(C_1$-$C_6)$alkyl group
a lipohilic chain selected in the group comprising, but not limited to, hexadecyloxypropyl (HDP)-, octadecyloxyethyl-, oleyloxypropyl-, and oleyloxyethyl-esters) with the proviso that when n=0 then R is not the cis-propenyl

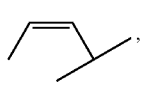, or
R' and R" form with the phosphate atom to which they are linked a cycloalkyle group of formula (4)

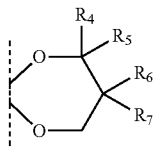

(4)

wherein $R_4$, $R_5$, $R_6$, et $R_7$ each independently represent a straight or branched $(C_1$-$C_6)$alkyl or aryl group or $R_4$, and $R_7$ independently represent a straight or branched $(C_1$-$C_6)$alkyl or aryl group or $R_5$ and $R_6$ form together an aromatic ring, said aromatic ring being optionally substituted for example by a chloride atom
with the proviso that

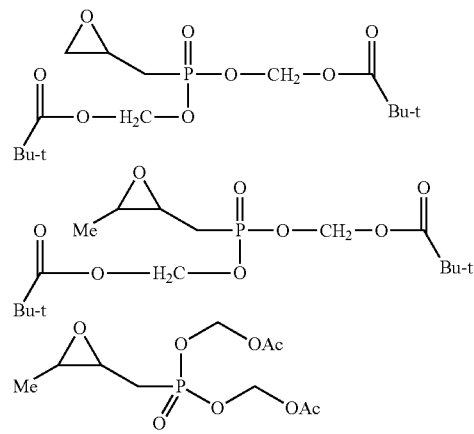

are excluded.
In an advantageous embodiment of the invention, the compounds are those of formula

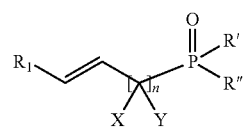

(I-1)

corresponding to a compound of formula (I) wherein

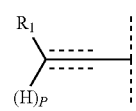

is a group

with $R_1$ is as defined before.
In another advantageous embodiment of the invention the compounds are those of formula

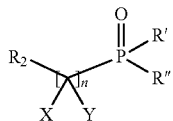

(I-2)

corresponding to a compound of formula (I) wherein R is equal to $R_2$ as defined above.

More advantageously, the compounds are selected from the group comprising

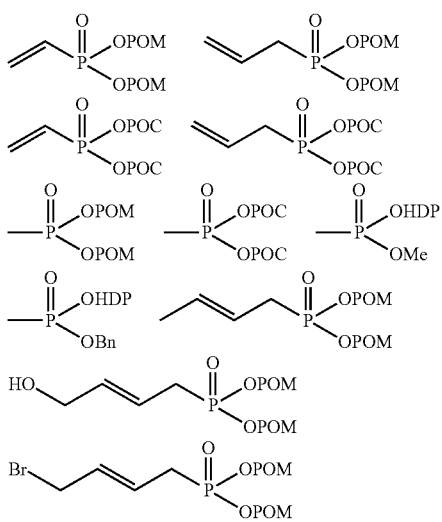

or from the group comprising

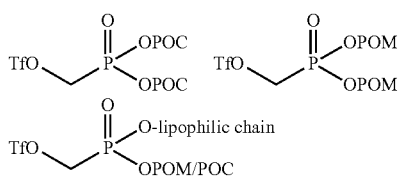

The compounds according to the invention may be prepared by any methods known from the one skilled in the art.

Another object of the invention is a process for making lipophilic pro-drugs comprising the step of contacting a drug D with a compound of formula (I) according to the invention.

In an advantageous embodiment of the invention, said process is an olefin-metathesis reaction comprising the step of contacting at least one compound of formula (I), with a drug D which bears an olefin group as shown in the following scheme

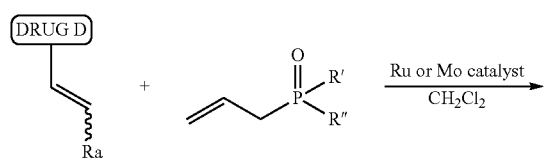

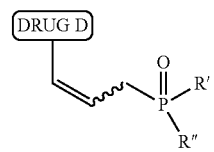

In an advantageous embodiment of the invention, said process is the step of contacting at least one compound according to anyone of claims 2, 4 and 5 with a drug D which bears a leaving group such as halogen, TfO, sulfones . . . .

In a more advantageous embodiment of the invention said process is a process for making a compound of formula (II-1)

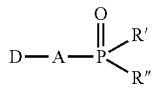

(II-1)

wherein
D is a drug which bears an olefin group,
A is a $(C_1-C_6)$alkenyl group comprising one or more double bonds,
R' and R" independently of each other
represent a group selected from the group comprising
an oxymethylcarbonyl group of formula (2)

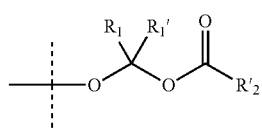

(2)

wherein
$R_1$ and $R'_1$ are independently of each other hydrogen or $(C_1-C_4)$alkyl group and
$R'_2$ is a straight or branched $(C_1-C_6)$alkyl group or straight or branched $(C_1-C_6)$alkoxy group
a thioethylcarbonyl group of formula (3)

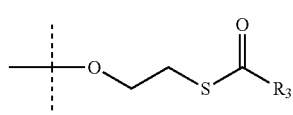

(3)

wherein
$R_3$ is a straight or branched $(C_1-C_6)$alkyl group
a lipohilic chain or
R' and R" forms with the phosphate atom to which they are linked a cycloalkyle group of formula (4)

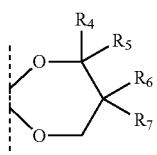

(4)

wherein $R_4$, $R_5$, $R_6$, et $R_7$ each independently represent a straight or branched ($C_1$-$C_6$)alkyl or aryl group or $R_4$, and $R_7$ independently represent a straight or branched ($C_1$-$C_6$)alkyl or aryl group or $R_5$ and $R_6$ form together an aromatic ring, said aromatic ring being optionally substituted for example by a chloride atom comprising the steps of:

a) providing a compound of formula (5)

$$D-A \qquad (5)$$

wherein A is a ($C_1$-$C_6$)alkenyl group comprising one or more double bonds b) reacting the compound of formula (5) with a compound of formula (I-1)

$$\text{(I-1)}$$

wherein R', R", $R_1$, n, X and Y are as defined in claim 2 to yield a compound of formula (II-1) and c) isolating the compound of formula (II-1).

In an advantageous embodiment of the invention the process is a process for making a compound of formula (II-2)

$$\text{(II-2)}$$

wherein m=0 ou 1

D is a drug,

R' and R" independently of each other represent a group selected from the group comprising an oxymethylcarbonyl group of formula (2)

$$\text{(2)}$$

wherein $R_1$ and $R'_1$ are independently of each other hydrogen or ($C_1$-$C_4$)alkyl group and $R'_2$ is a straight or branched ($C_1$-$C_6$)alkyl group or straight or branched ($C_1$-$C_6$)alkoxy group a thioethylcarbonyl group of formula (3)

$$\text{(3)}$$

wherein $R_3$ is a straight or branched ($C_1$-$C_6$)alkyl group a lipophilic chain or R' and R" forms with the phosphate atom to which they are linked a cycloalkyle group of formula (4)

$$\text{(4)}$$

wherein $R_4$, $R_5$, $R_6$, et $R_7$ each independently represent a straight or branched ($C_1$-$C_6$)alkyl or aryl group or $R_4$, and $R_7$ independently represent a straight or branched ($C_1$-$C_6$)alkyl or aryl group or $R_5$ and $R_6$ form together an aromatic ring, said aromatic ring being optionally substituted for example by a chloride atom comprising the steps of:

d) providing a compound of formula (6)

$$D-OH \qquad (6)$$

e) reacting in a nucleophilic substitution reaction the compound of formula (6) with a compound of formula (I-2)

$$\text{(I-2)}$$

wherein R', R", $R_2$, n, X and Y are as defined in claim 3 to yield a compound of formula (II-2) and f) isolating the compound of formula (II-2).

When D is a phosphonate derivative, the synthon according to the invention will be introduced by any reaction known from the one skilled in the art, for example by Diels and Alder reaction, Arbuzov reaction, olefin metathesis, nucleophilic substitution In another embodiment according to the invention, the prodrugs may be prepared by a Mitsunobu reaction of an alcohol according to the following scheme.

wherein R' and R" are as disclosed above

According to the invention, halogen stands for fluorine, chlorine, bromine and iodine.

The term straight or branched ($C_1$-$C_6$)alkyl group stands for a straight-chain or branched hydrocarbon residue containing 1-6 C-atoms, such as, methyl, ethyl, propyl, isopropyl, n-butyl, isobutyl, t-butyl, n-hexyl.

The term ($C_1$-$C_6$)alkoxy group stands for alkyl-O— with alkyl as defined above, e.g. methoxy, ethoxy, n-propoxy, iso-propoxy, n-butoxy, isobutoxy, t-butoxy and hexoxy.

The term straight or branched ($C_2$-$C_6$)alkenyl groups stands for straight-chain or branched hydrocarbon residue containing one or more olefinic bonds and up to 6, preferably up to 4 C-atoms. Olefin and olefine may also be used to design an alkenyl group.

The term lipophilic chain or long-chain refers to the cyclic, branched or straight chain chemical groups that when covalently linked to a phosphonic acid to form a phosphonate ester increase oral bioavailability and enhance activity as for instance for some nucleoside phosphonates when compared with the parent nucleoside. These lipophilic groups include, but are not limited to aryl, alkyl, alkoxyalkyl, and alkylglyceryl (such as hexadecyloxypropyl (HDP)-, octadecyloxyethyl-, oleyloxypropyl-, and oleyloxyethyl-esters).

The term aromatic ring stands for, but is not limited to aryl, e.g. phenyl, benzyl, naphtyl or indanyl, said aryl group being optionally substituted.

The term leaving groups is an ion (metal) or substituent with the ability to detach itself from a molecule e.g. halogen, sulfonyl group for example p-toluensulfonyloxy group and the like.

The term carbonyl group stands for a group composed of a carbon atom double-bonded to an oxygen atom: C=O e.g. formyl, acetyl, propionyl, butyryl and the like.

D is selected from a compound having a biological activity such as but not limited to neurotransmitters, stimulants, dopaminergic agents, tranquilizers, antidepressants, narcotic analgesics, narcotic antagonists, sedatives, hypnotics, anesthetics, antiepileptics/anticonvulsants, hormones such as the male and female sex hormones, peptides, anti-inflammatory steroids, non-steroidal anti-inflammatory agents/non-narcotic analgesics, memory enhancers, antibacterials/antibiotics, antineoplastics (anticancer/antitumor agents) and antiviral agents.

POM states for pivaloyl oxymethyl and POC states for isopropyloxymethylcarbonate. Molecules bearing bis-POM and/or bisPOC are directly usable to be biologically tested. Molecules bearing a HDP group should be first deprotected before being tested.

Another object of the invention is the use of compounds according to the invention as intermediates in the synthesis of phosphonates derivatives useful as pro-drugs.

Another object of the invention are compounds of formula

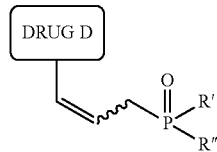

for their use as drugs, in particular the compounds of examples 16 to 48.

Still another object of the invention is a method of treating a disease comprising the administration to a patient in need thereof of a compound of formula

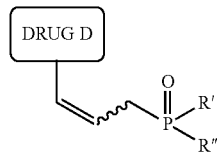

Another object of the invention is a method of making phosphonates derivatives useful as pro-drugs comprising a step involving the compounds according to the invention as intermediates.

Thus with the synthons according to the invention, it is possible to synthesize bis-POM/POC acyclonucleosides phosphonates prodrugs by direct Cross Metathesis of allyl bis-POM/POC allylphosphonates, on free nucleosides. They permit to introduce in a same step the phosphorus and the POM/POC prodrug part.

The following figures and examples are provided for illustrative purposes.

Examples 1 to 15 illustrate the synthesis of the synthons according to the invention.

Examples 16 to 48 illustrate the synthesis of prodrugs from said synthons.

FIG. 1 presents the Log D i.e. the logarithm of the water/octanol partition ratio at pH=7.4 as measured according to example 49.

EXAMPLE 1

General Procedures 1.1. Introduction of Lipophilic Chain on Dialkyl Alkylphosphonate To a dichloromethane (DCM) (5 mL/mmol) solution of dialkyl allylphosphonate (1 eq.) was added oxalyl chloride (3 eq.), and gently reflux for 24 h under positive pressure of dry argon. This solution was evaporated under reduced pressure and diluted in DCM (5 mL/mmol). Lipophilic alcohol (1.05 eq.) and dry triethylamine (1.5 eq.) were then added and the solution was refluxed for 48 h under positive pressure of dry argon. Volatiles were evaporated and the residue purified by chromatography on silica gel to give the corresponding alkyl/lipophilic chain alkylphosphonate.

1.2. Conversion of Dimethyl Alkylphosphonate into Bis-(POM) or Bis-(POC) Form.

To an acetonitrile ACN (1 mL/mmol) solution of dimethyl alkylphosphonate (1 eq.) and anhydrous sodium iodide (2 eq.), was added chloromethyl pivalate POMC1 (2.5 eq.) or chloromethyl isopropyl carbonate (2.5 eq.). This solution was stirred at reflux for 48 h under positive pressure of dry argon. After cooling, diethyl ether was added (10 mL/mmol) and the solution was washed with water (2 mL/mmol). The organic layer was dried on magnesium sulfate, evaporated and purified by chromatography on silica gel to give the corresponding Bis-(POM) or Bis-(POC) alkylphosphonate.

1.3. Conversion of Methyl/Prodrug Group Alkylphosphonate into Mixt POM or POC/Prodrug Group Alkylphosphonate To an ACN (1 mL/mmol) solution of methyl/prodrug group alkylphosphonate (1 eq.) and anhydrous sodium iodide (1 eq.), was added chloromethyl pivalate POMC1 (1.5 eq.) or chloromethyl isopropyl carbonate (1.5 eq.). This solution was stirred at reflux for 48 h under positive pressure of dry argon. After cooling, diethyl ether was added (10 mL/mmol) and the solution was washed by water (2 mL/mmol). The organic layer was dried on magnesium sulfate, evaporated and purified by chromatography on silica gel to give corresponding Bis-(POM) or Bis-(POC) alkylphosphonate.

1.4. Conversion of Dialkyl H-Phosphonate into Alkyl/Lipophilic Chain H-Phosphonate.

To a tetrahydrofuran (THF) (1 mL/mmol) solution of 1,3-bis(cyclcohexyl) imidazolium tetrafluoroborate (IcyHBF$_4$) salt (0.05 eq.) and molecular sieves (0.5 g/mmol), under argon, is added tBuOK (0.9 eq.) and stirred for 10 min.

Lipophilic alcohol (1 eq.) and dialkyl H-phosphonate (2 eq.) are added and the reaction stirred at room temperature for 24 h. The reaction is quenched with a saturated solution of ammonium chloride (5 mL/mmol) and filtrate on celite. Ethylacetate (AcOEt) (10 mL/mmol) is added to the solution then the organic and aqueous layers are separated. Aqueous phase is then extracted with AcOEt (10 mL/mmol) and the combinated organic layers are evaporated under vacuum. The corresponding alkyl/lipophilic chain H-phosphonate is finally purified by chromatography on silica gel.

EXAMPLE 2

Synthesis of Bn/HDP H-Phosphonate

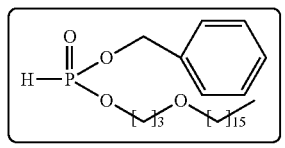

1

Compound 1 is synthesized according to procedure 1.4. from dibenzylphosphite as reported by the scheme 1.

Scheme 1

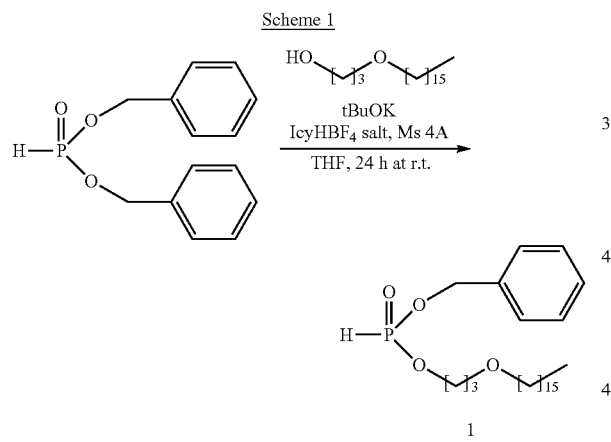

1

$^1$H NMR (400 MHz, CDCl$_3$) δ=7.74 (s, 0.5H, H—P), 7.41-7.33 (m, 5H, H$_{Ar}$), 5.99 (s, 0.5H, H—P), 5.11 (d, J=9.5 Hz, 3H, OCH$_3$), 4.20-4.07 (m, 2H, P—O—CH$_2$—CH$_2$—CH$_2$—O), 3.46 (t, J=6.1 Hz, 2H, P—O—CH$_2$—CH$_2$—CH$_2$—O), 3.37 (t, J=6.7 Hz, 2H, O—CH$_2$—CH$_2$—(CH$_2$)$_{13}$—CH$_3$), 1.90 (p, J=6.2 Hz, 2H, P—O—CH$_2$—CH$_2$—CH$_2$—O), 1.53 (p, J=6.9 Hz, 2H, O—CH$_2$—CH$_2$—(CH$_2$)$_{13}$—CH$_3$), 1.35-1.19 (m, 26H, O—CH$_2$—CH$_2$—(CH$_2$)$_{13}$—CH$_3$), 0.87 (t, J=6.4 Hz, 3H, O—CH$_2$—CH$_2$—(CH$_2$)$_{13}$—CH$_3$).

$^{13}$C NMR (100 MHz, CDCl$_3$) δ=136.6, 128.7, 128.6, 127.9, 126.9 (C$_{Ar}$), 71.2 (O—CH$_2$—CH$_2$—(CH$_2$)$_{13}$—CH$_3$), 67.2 (2C, CH$_2$-Ph), 66.3 (P—O—CH$_2$—CH$_2$—CH$_2$—O), 63.1, 63.0 (P—O—CH$_2$—CH$_2$—CH$_2$—O), 31.9, 30.6 (2C), 29.7, 29.6 (2C), 29.5, 29.3, 26.1, 22.7 (CH$_2$—P, P—O—CH$_2$—CH$_2$—CH$_2$—O, O—CH$_2$—CH$_2$—(CH$_2$)$_{13}$—CH$_3$), 14.1 (O—CH$_2$—CH$_2$—(CH$_2$)$_{13}$—CH$_3$).

$^{31}$P NMR (162 MHz, CDCl$_3$): δ=10.05.

EXAMPLE 3

Synthesis of Bis-(POM) Methylphosphonate

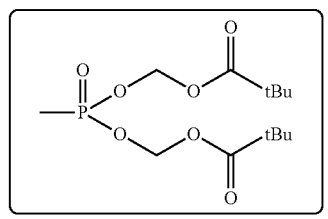

2

Compound 2 is synthesized according to procedure 1.2. from dimethyl methylphosphonate as reported by the scheme 2

Scheme 2

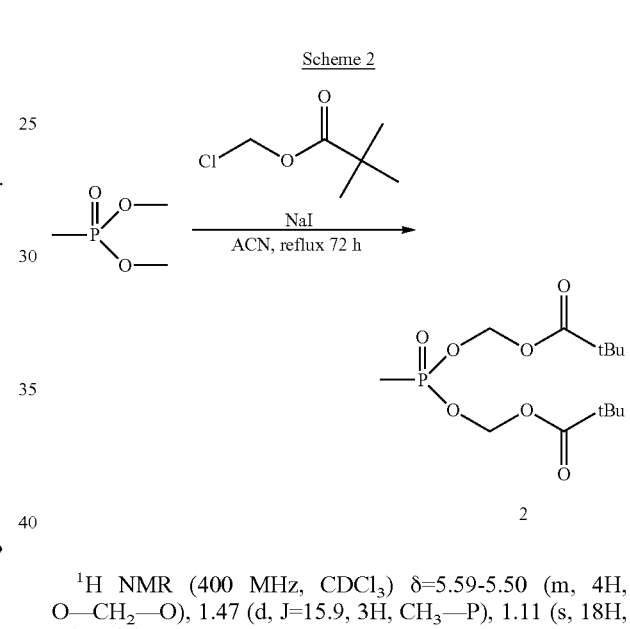

2

$^1$H NMR (400 MHz, CDCl$_3$) δ=5.59-5.50 (m, 4H, O—CH$_2$—O), 1.47 (d, J=15.9, 3H, CH$_3$—P), 1.11 (s, 18H, C(CH$_3$)$_3$).

$^{13}$C NMR (100 MHz, CDCl$_3$) δ=176.5 (C=O), 81.1, 81.0 (O—CH$_2$—O), 38.4 (C(CH$_3$)$_3$), 26.6 (C(CH$_3$)$_3$), 12.9, 11.5 (CH$_3$—P).

$^{31}$P NMR (162 MHz, CDCl$_3$): δ=31.54

EXAMPLE 4

Synthesis of HDP/Bn Methylphosphonate

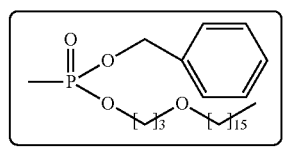

3

Compound 3 is synthesized according to procedure 1.1. from dibenzyl methylphosphonate as reported by the scheme 3.

Scheme 3

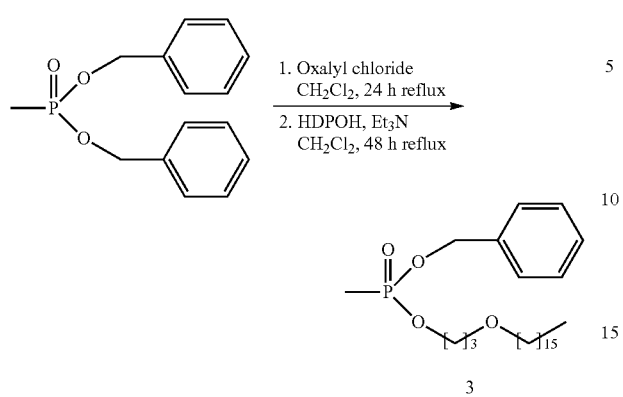

¹H NMR (400 MHz, CDCl₃) δ=7.41-7.28 (m, 1H), 5.11-4.99 (m, 2H, CH₂-Ph), 4.15-3.99 (m, 2H, P—O—CH₂—CH₂—CH₂—O), 3.45 (t, J=6.3 Hz, 2H, P—O—CH₂—CH₂—CH₂—O), 3.36 (t, J=6.7 Hz, 2H, O—CH₂—CH₂—(CH₂)₁₃—CH₃), 1.87 (p, J=6.3 Hz, 2H, P—O—CH₂—CH₂—CH₂—O), 1.53 (p, J=6.9 Hz, 2H, O—CH₂—CH₂—(CH₂)₁₃—CH₃), 1.46 (d, J=17.6 Hz, 3H, CH₃—P), 1.32-1.20 (m, 26H, O—CH₂—CH₂—(CH₂)₁₃—CH₃), 0.87 (t, J=6.4 Hz, 3H, O—CH₂—CH₂—(CH₂)₁₃—CH₃).

¹³C NMR (100 MHz, CDCl₃) δ=136.4 (2C), 128.5, 128.3, 127.8 (C_Ar), 71.2 (O—CH₂—CH₂—(CH₂)₁₃—CH₃), 67.0 (2C, CH₂-Ph), 66.5 (P—O—CH₂—CH₂—CH₂—O), 62.9, 62.8 (P—O—CH₂—CH₂—CH₂—O), 31.9, 30.8, 30.7, 30.3 (2C), 29.7, 29.6 (3C), 29.5, 29.3, 26.1, 22.6 (CH₂—P, P—O—CH₂—CH₂—CH₂—O, O—CH₂—CH₂—(CH₂)₁₃—CH₃), 14.1 (O—CH₂—CH₂—(CH₂)₁₃—CH₃), 11.9, 10.4 (CH₃—P).

³¹P NMR (162 MHz, CDCl₃): δ=31.23

EXAMPLE 5

Synthesis of Bis-(POC) Vinylphosphonate

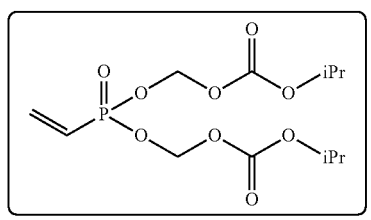

Compound 4 is synthesized according to procedure 1.2. from dimethyl vinylphosphonate as reported by the scheme 4.

Scheme 4

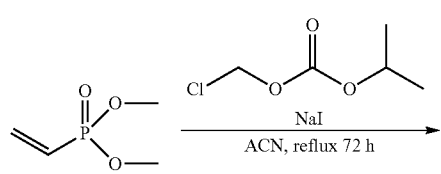

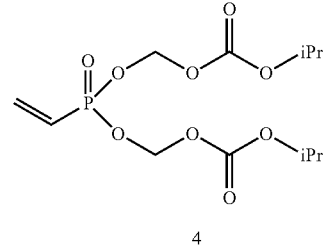

¹H NMR (400 MHz, CDCl₃): δ=6.45-6.03 (m, 3H, CH₂=CH), 5.72-5.63 (m, 4H, O—CH₂—O), 4.92 (sept., J=6.2 Hz, 2H, CH(CH₃)₂), 1.31 (d, J=6.3 Hz, 12H, CH(CH₃)₂).

¹³C NMR (100 MHz, CDCl₃): δ=153.1 (C=O), 136.9, 136.8 (CH₂=CH), 125.6, 123.7 (CH₂=CH), 84.1, 84.0 (O—CH₂—O), 73.2 (CH(CH₃)₂), 21.6 (CH(CH₃)₂).

³¹P NMR (162 MHz, CDCl₃): δ=16.89.

EXAMPLE 6

Synthesis of Bis-(POM) Vinylphosphonate

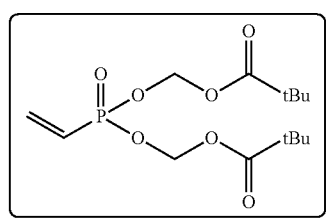

Compound 5 is synthesized according to procedure 1.2. from dimethyl vinylphosphonate as reported by the scheme 5

Scheme 5

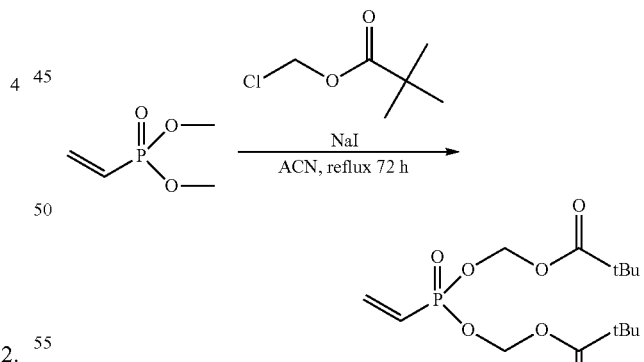

¹H NMR (400 MHz, CDCl₃) δ=6.43-5.99 (m, 3H, CH₂=CH), 5.74-5.60 (m, 4H, O—CH₂—O), 1.21 (s, 18H, C(CH₃)₃).

¹³C NMR (100 MHz, CDCl₃) δ=176.7 (C=O), 136.6 (2C, CH₂=CH), 126.0, 124.1 (CH₂=CH), 81.5, 81.4 (O—CH₂—O), 38.7, 38.4 (C(CH₃)₃), 27.0, 26.8 (C(CH₃)₃).

³¹P NMR (162 MHz, CDCl₃) δ=17.14.

EXAMPLE 7

Synthesis of Me/HDP Vinylphosphonate

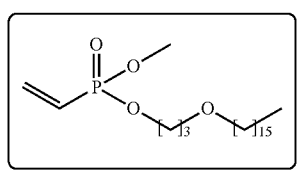

Compound 6 is synthesized according to procedure 1.1. from dimethyl vinylphosphonate as reported by the scheme 6.

Scheme 6

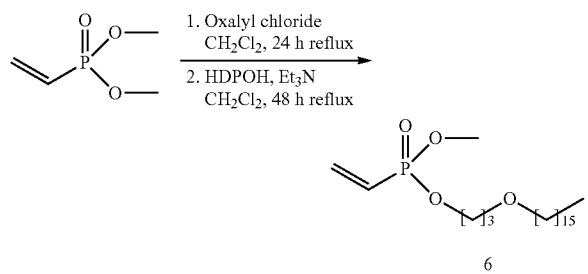

$^1$H NMR (400 MHz, CDCl$_3$): δ=6.37-5.93 (m, 3H, CH$_2$=CH), 4.11 (q, J=6.5 Hz, 2H, P—O—CH$_2$—CH$_2$—CH$_2$—O), 3.70 (d, J=11.1 Hz, 3H, OCH$_3$), 3.48 (t, J=6.1 Hz, 2H, P—O—CH$_2$—CH$_2$—CH$_2$—O), 3.37 (t, J=6.7 Hz, 2H, O—CH$_2$—CH$_2$—(CH$_2$)$_{13}$—CH$_3$), 1.92 (p, J=6.3 Hz, 2H, P—O—CH$_2$—CH$_2$—CH$_2$—O), 1.57-1.49 (p, J=6.9 Hz, 2H, O—CH$_2$—CH$_2$—(CH$_2$)$_{13}$—CH$_3$), 1.34-1.20 (m, 26H, O—CH$_2$—CH$_2$—(CH$_2$)$_{13}$—CH$_3$), 0.86 (t, J=6.8 Hz, 3H, O—CH$_2$—CH$_2$—(CH$_2$)$_{13}$—CH$_3$).

$^{13}$C NMR (100 MHz, CDCl$_3$) δ=136.0 (2C, CH$_2$=CH), 126.0, 124.1 (CH$_2$=CH), 71.2 (O—CH$_2$—CH$_2$—(CH$_2$)$_{13}$—CH$_3$), 66.5 (P—O—CH$_2$—CH$_2$—CH$_2$—O), 63.2 (2C, P—O—CH$_2$—CH$_2$—CH$_2$—O), 52.3 (2C, OCH$_3$), 31.9, 30.8 (2C), 29.7, 29.6 (3C), 29.5, 29.3, 26.1, 22.6 (CH$_2$—P, P—O—CH$_2$—CH$_2$—CH$_2$—O, O—CH$_2$—CH$_2$—(CH$_2$)$_{13}$—CH$_3$), 14.1 (O—CH$_2$—CH$_2$—(CH$_2$)$_{13}$—CH$_3$).

$^{31}$P NMR (162 MHz, CDCl$_3$): δ=18.80.

EXAMPLE 8

Synthesis of Bis-(POM) Allylphosphonate

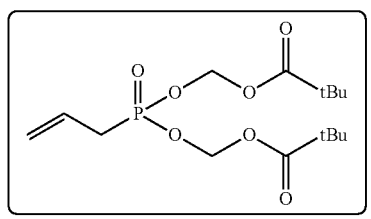

Compound 7 is synthesized according to procedure 1.2. from dimethyl allylphosphonate as reported by the scheme 7.

Scheme 7

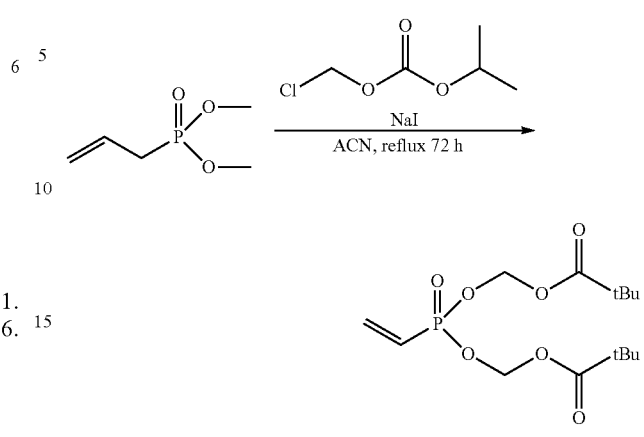

$^1$H NMR (400 MHz, CDCl$_3$) δ=5.74-5.57 (m, 5H, O—CH$_2$—O, CH$_2$=CH), 5.22-5.14 (m, 2H, CH$_2$=CH), 2.64 (dd, J=22.6 Hz, J=7.3 Hz, 2H, P—CH$_2$), 1.16 (s, 18H, C(CH$_3$)$_3$).

$^{13}$C NMR (100 MHz, CDCl$_3$) δ=176.6 (C=O), 125.8, 125.7 (CH$_2$=CH), 121.0, 120.9 (CH$_2$=CH), 81.4, 81.3 (O—CH$_2$—O), 38.6 (C(CH$_3$)$_3$), 32.7, 31.3 (CH$_2$—P), 26.7 (C(CH$_3$)$_3$).

$^{31}$P NMR (162 MHz, CDCl$_3$) δ=27.71.

EXAMPLE 9

Synthesis of Bis-(POC) Allylphosphonate

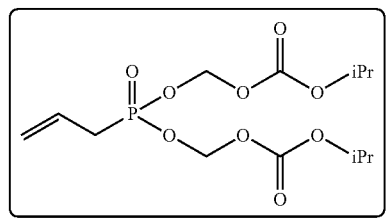

Compound 8 is synthesized according to procedure 1.2. from dimethyl allylphosphonate as reported by the scheme 8

Scheme 8

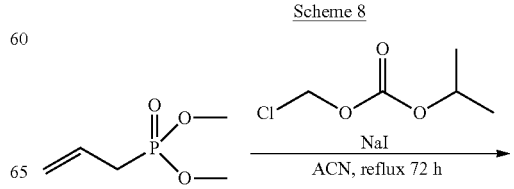

-continued

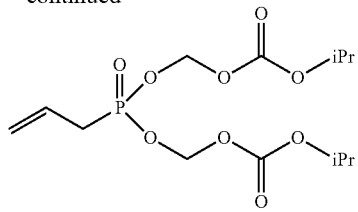

8

$^1$H NMR (400 MHz, CDCl$_3$) δ=5.82-5.71 (m, 1H, CH$_2$=CH), 5.68 (dd, 2H, J=5.4 Hz, 11.6 Hz, O—CH$_2$—O), 5.65 (dd, 2H, J=5.4 Hz, 11.6 Hz, O—CH$_2$—O), 5.30-5.22 (m, 2H, CH$_2$=CH), 4.94 (sept., J=6.2 Hz, 2H, CH(CH$_3$)$_2$), 2.74 (tdd, J=22.8, 7.4, 1.1 Hz, 2H, P—CH$_2$), 1.33 (d, J=6.28 Hz, 12H, CH(CH$_3$)$_2$).

$^{13}$C NMR (100 MHz, CDCl$_3$) δ=153.2 (C=O), 125.7, 125.6 (CH$_2$=CH), 121.3, 121.2 (CH$_2$=CH), 84.1, 84.0 (O—CH$_2$—O), 73.2 (CH(CH$_3$)$_2$), 32.9, 31.5 (CH$_2$—P), 21.6 (CH(CH$_3$)$_2$).

$^{31}$P NMR (162 MHz, CDCl$_3$): δ=27.99.

EXAMPLE 10

Synthesis of Me-HDP Allylphosphonate

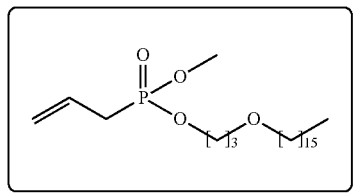

9

Compound 9 is synthesized according to procedure 1.1. from dimethyl allylphosphonate as reported by the scheme 9.

Scheme 9

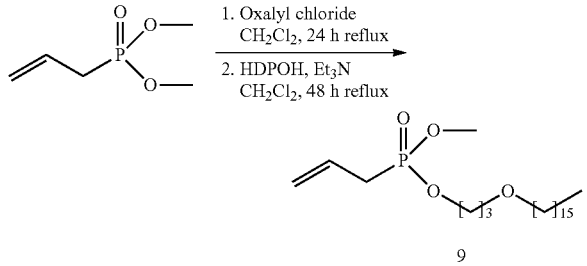

9

$^1$H NMR (400 MHz, CDCl$_3$) δ=5.85-5.71 (m, 1H, CH$_2$=CH), 5.26-5.16 (m, 2H, CH$_2$=CH), 4.13 (dt, J=6.5, 1.7 Hz, 2H, P—O—CH$_2$—CH$_2$—CH$_2$—O), 3.73 (d, J=10.9 Hz, 3H, OCH$_3$), 3.48 (t, J=6.2 Hz, 2H, P—O—CH$_2$—CH$_2$—CH$_2$—O), 3.38 (t, J=6.7 Hz, 2H, O—CH$_2$—CH$_2$—(CH$_2$)$_{13}$—CH$_3$), 2.62 (ddt, J=22.0, 7.4, 1.1 Hz, 2H, CH$_2$—P), 1.91 (p, J=6.3 Hz, 2H, P—O—CH$_2$—CH$_2$—CH$_2$—O), 1.54 (p, J=6.9 Hz, 2H, O—CH$_2$—CH$_2$—(CH$_2$)$_{13}$—CH$_3$), 1.32-1.22 (m, 26H, O—CH$_2$—CH$_2$—(CH$_2$)$_{13}$—CH$_3$), 0.86 (t, J=6.8 Hz, 3H, O—CH$_2$—CH$_2$—(CH$_2$)$_{13}$—CH$_3$).

$^{13}$C NMR (100 MHz, CDCl$_3$) δ=127.3, 127.2 (CH$_2$=CH), 120.1, 120.0 (CH$_2$=CH), 71.2 (O—CH$_2$—CH$_2$—(CH$_2$)$_{13}$—CH$_3$), 66.5 (P—O—CH$_2$—CH$_2$—CH$_2$—O), 63.3 (2C, P—O—CH$_2$—CH$_2$—CH$_2$—O), 52.6, 52.5 (OCH$_3$), 31.9, 31.8, 30.9, 30.8, 30.4, 29.7, 29.6 (3C), 29.5, 29.3, 26.1, 22.7 (CH$_2$—P, P—O—CH$_2$—CH$_2$—CH$_2$—O, O—CH$_2$—CH$_2$—(CH$_2$)$_{13}$—CH$_3$), 14.1 (O—CH$_2$—CH$_2$—(CH$_2$)$_{13}$—CH$_3$).

$^{31}$P NMR (162 MHz, CDCl$_3$) δ=28.3.

EXAMPLE 11

Synthesis of HDP-POC Allylphosphonate

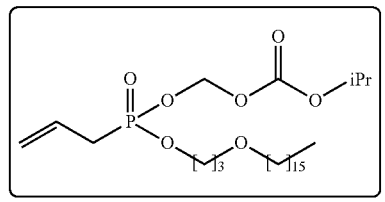

10

Compound 10 is synthesized according to procedure 1.3. from methyl HDP allylphosphonate obtained in example 9, as reported by the scheme 10.

Scheme 10

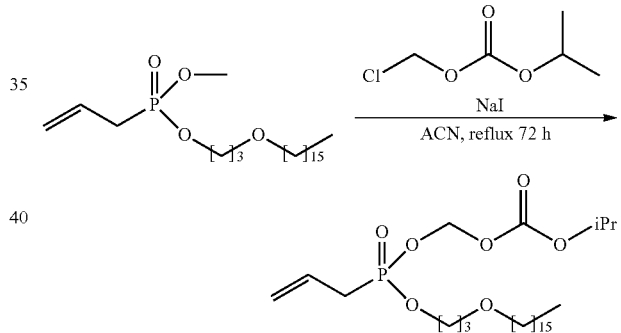

10

$^1$H NMR (400 MHz, CDCl$_3$) δ=5.82-5.68 (m, 1H, CH$_2$=CH), 5.68-5.58 (m, 1H, O—CH$_2$—O), 5.26-5.17 (m, 2H, CH$_2$=CH), 4.91 (sept., J=6.3 Hz, 2H, CH(CH$_3$)$_2$), 4.24-4.07 (m, 2H, P—O—CH$_2$—CH$_2$—CH$_2$—O), 3.47 (t, J=6.2 Hz, 2H, P—O—CH$_2$—CH$_2$—CH$_2$—O), 3.37 (t, J=6.7 Hz, 2H, O—CH$_2$—CH$_2$—(CH$_2$)$_{13}$—CH$_3$), 2.67 (dd, J=22.4, 7.4 Hz, 2H, CH$_2$—P), 1.91 (p, J=6.3 Hz, 2H, P—O—CH$_2$—CH$_2$—CH$_2$—O), 1.57-1.49 (p, J=6.9 Hz, 2H, O—CH$_2$—CH$_2$—(CH$_2$)$_{13}$—CH$_3$), 1.33-1.20 (m, 32H, O—CH$_2$—CH$_2$—(CH$_2$)$_{13}$—CH$_3$, CH(CH$_3$)$_2$), 0.86 (t, J=6.7 Hz, 3H, O—CH$_2$—CH$_2$—(CH$_2$)$_{13}$—CH$_3$)

$^{13}$C NMR (100 MHz, CDCl$_3$) δ=153.2 (C=O), 126.6, 126.5 (CH$_2$=CH), 120.6, 120.5 (CH$_2$=CH), 84.4, 84.3 (O—CH$_2$—O), 73.0, 71.2 (CH(CH$_3$)$_2$), 66.5 (P—O—CH$_2$—CH$_2$—CH$_2$—O), 63.3 (2C, P—O—CH$_2$—CH$_2$—CH$_2$—O), 32.7, 31.9, 31.3, 30.7 (2C), 29.7, 29.6 (2C), 29.5, 29.3, 26.1, 22.7, 21.6 (CH(CH$_3$)$_2$, P—O—CH$_2$—CH$_2$—CH$_2$—O, O—CH$_2$—CH$_2$—(CH$_2$)$_{13}$—CH$_3$), 14.1 (O—CH$_2$—CH$_2$—(CH$_2$)$_{13}$—CH$_3$).

$^{31}$P NMR (162 MHz, CDCl$_3$) δ=26.7.

EXAMPLE 12

Bis-(POM)hydroxymethylphosphonate

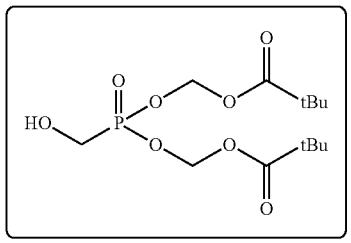

12

12.1. Synthesis of Bis-(POM)benzyloxymethylphosphonate

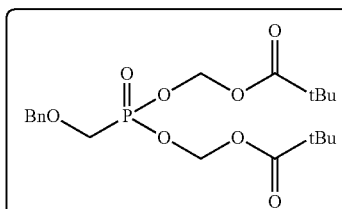

11

Compound 11 is synthesized according to procedure 1.2. from dimethylbenzyloxyphosphonate, as reported by the scheme 11.

Scheme 11

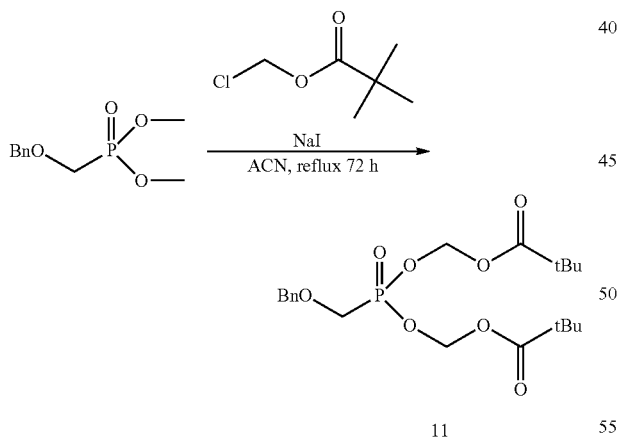

11

$^1$H NMR (400 MHz, CDCl$_3$) δ=7.40-7.26 (m, 5H, H$_{Ar}$), 5.74-5.68 (d, J=12.7 Hz, 4H, O—CH$_2$—O), 4.64 (s, 2H, Ph-CH$_2$), 3.83 (d, J=8.2 Hz, 2H, O—CH$_2$—P), 1.22 (s, 18H, C(CH$_3$)$_3$).

$^{13}$C NMR (100 MHz, CDCl$_3$) δ=176.7 (C═O), 136.5, 128.4, 128.1, 128.0 (C$_{Ar}$), 81.6 (2C, O—CH$_2$—O), 75.0, 74.9 (Ph-CH$_2$), 64.7, 63.0 (O—CH$_2$—P), 38.6 (C(CH$_3$)$_3$), 26.7 (C(CH$_3$)$_3$).

$^{31}$P NMR (162 MHz, CDCl$_3$) δ=21.79.

12.2. Synthesis of Bis-(POM)hydroxymethylphosphonate

Compound 12 is synthesized according to the following scheme 12.

Scheme 12

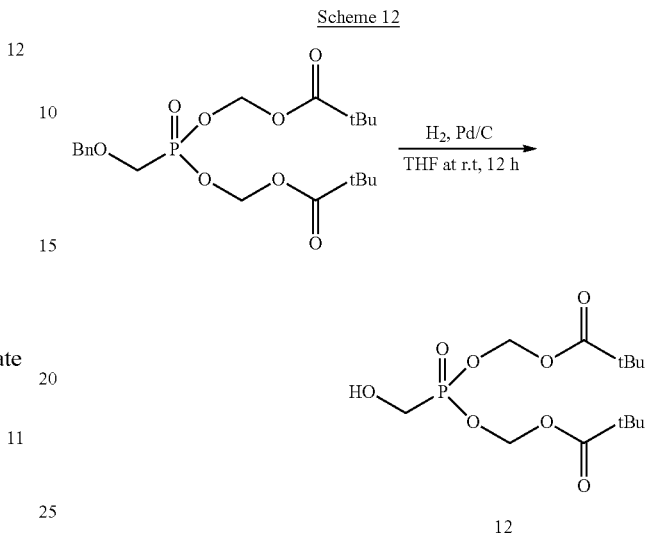

12

To a THF (5 mL/mmol) solution of bis-(POM)benzyloxymethylphosphonate prepared according to example 11.1. is added 5% Pd on activated carbon (0.05 eq. of Pd), and stirred under an hydrogen atmosphere for 12 h. The mixture is then filtrated, evaporated and purified by chromatography on silica gel (50% AcOEt/EP) to give pure bis-(POM)hydroxymethylphosphonate.

$^1$H NMR (400 MHz, CDCl$_3$) δ ppm 5.72-5.55 (m, 4H, O—CH$_2$—O), 3.97 (d, J=5.3 Hz, 2H, O—CH$_2$—P), 1.22 (s, 18H, (C(CH$_3$)$_3$).

$^{13}$C NMR (100 MHz, CDCl$_3$) δ ppm 177.0 (C═O), 81.8, 81.7 (O—CH$_2$—O), 58.2, 56.6 (O—CH$_2$—P), 38.7 (C(CH$_3$)$_3$), 26.8 (C(CH$_3$)$_3$).

$^{31}$P NMR (162 MHz, CDCl$_3$) δ=24.07.

EXAMPLE 13

Synthesis of Bis-(POM) 1-hydroxymethyl-allylphosphonate

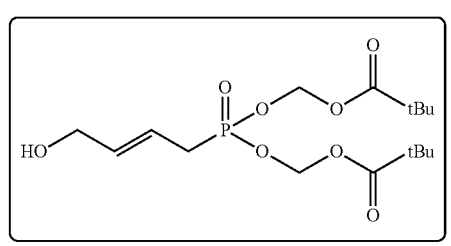

13

Compound 13 is synthesized according to the following scheme 14 from compound 7 as reported by the scheme 13.

Scheme 13

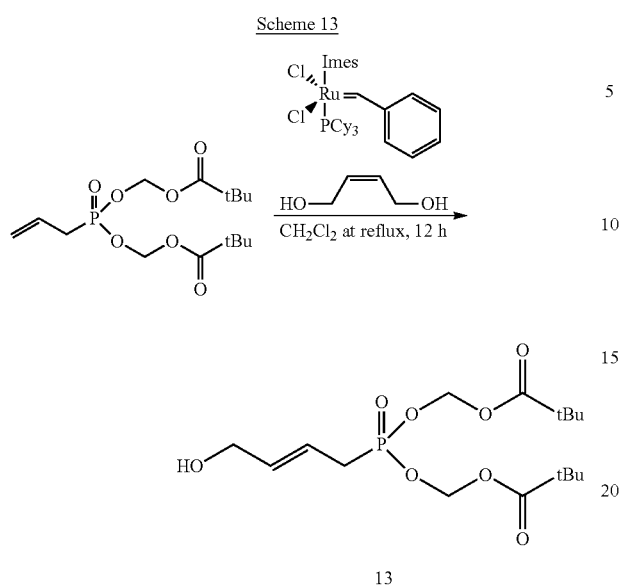

To a dichloromethane (20 mL/mmol) solution of bis-(POM)allylphosphonate and 2-buten-1,4-diol under argon is added ImesRuCl$_2$(PPh$_3$)$_2$ (0.05 eq.) and reflux for 12 h. After evaporation of all volatiles, the residue is purified by chromatography on silica gel (50% AcOEt/EP) to give pure bis-(POM) 1-hydroxymethyl-allylphosphonate.

$^1$H NMR (400 MHz, CDCl$_3$) δ ppm=5.88-5.79 (m, 1H, CH=CH), 5.73-5.55 (m, 5H, CH=CH, O—CH$_2$—O), 4.11 (t, J=7.4 Hz, HOCH$_2$, 2H), 2.68 (dd, J=22.4, 7.3 Hz, 2H, CH$_2$—P), 2.03 (s, 1H, OH), 1.22 (s, 18H, C(CH$_3$)$_3$).

$^{13}$C NMR (100 MHz, CDCl$_3$) δ ppm=176.9 (C=O), 135.9, 135.7 (CH=CH), 119.0, 118.9 (CH=CH), 81.6, 81.5 (O—CH$_2$—O), 62.9 (2C, HOCH$_2$), 38.7 (C(CH$_3$)$_3$), 31.4, 30.1 (CH$_2$—P), 26.8 (C(CH$_3$)$_3$).

$^{31}$P NMR (162 MHz, CDCl$_3$): δ=27.54.

EXAMPLE 14

Synthesis of Bis-(POM) 1-bromomethyl-allyl phosphonate

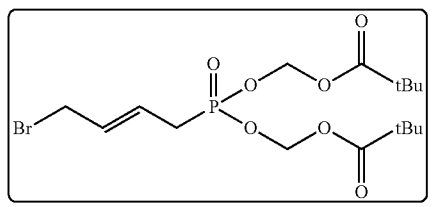

Compound 14 is synthesized according to the following scheme 14 from compound 7.

Scheme 14

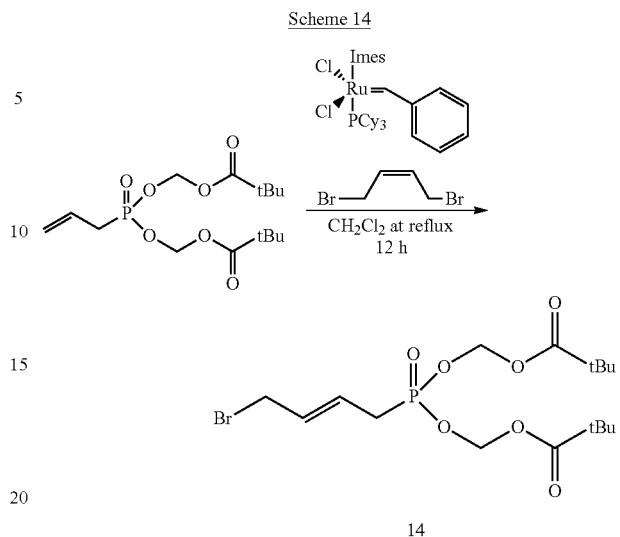

$^1$H NMR (400 MHz, CDCl$_3$) δ ppm=5.93-5.83 (m, 1H, CH=CH), 5.74-5.62 (m, 5H, CH=CH, O—CH$_2$—O), 3.92 (dd, J=7.5, 3.5 Hz, BrCH$_2$, 2H), 2.70 (dd, J=22.7, 7.3 Hz, CH$_2$—P, 2H), 1.23 (s, 18H, C(CH$_3$)$_3$).

$^{13}$C NMR (100 MHz, CDCl$_3$) δ ppm=176.9 (C=O), 135.9, 135.7 (CH=CH), 119.0, 118.9 (CH=CH), 81.6, 81.5 (O—CH$_2$—O), 62.9 (2C, HOCH$_2$), 38.7 (C(CH$_3$)$_3$), 31.4, 30.1 (CH$_2$—P), 26.8 (C(CH$_3$)$_3$).

$^{31}$P NMR (162 MHz, CDCl$_3$): δ=26.77.

EXAMPLE 15

Synthesis of Bis-(POM) Trifluoromethanesulfonic Oxymethylphosphonate

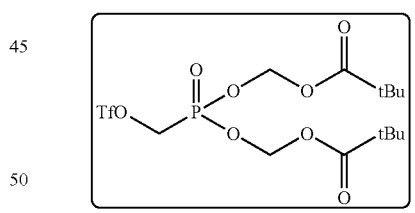

Compound 15 is synthesized according to the following scheme 15 from compound 12.

Scheme 15

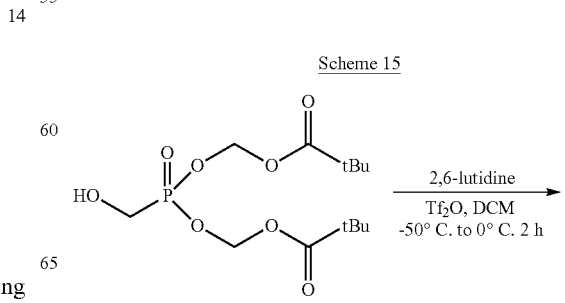

23
-continued

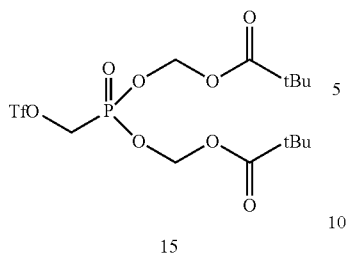

To a dichloromethane (2 mL/mmol) solution of bis-(POM) hydroxymethylphosphonate obtained in example 12.2 and 2,6 lutidine under argon is added trifluoromethanesulfonic anhydride at −50° C. at stirred 10 minutes. The mixture is then allowed to warm to 0° C. and stirred for 2 h. The mixture is then diluted in diethyl ether (15 ml/mmol), washed with water (5 mL/mmol). After evaporation of volatiles, the residue is purified by chromatography on silica gel (15% AcOEt/EP) to give pure bis-(POM) trifluoromethanesulfonic oxymethylphosphonate.

1H NMR (400 MHz, CDCl$_3$) δ=5.78 (dd, J=12.1, 5.2 Hz, 2H), 5.69 (dd, J=12.1, 5.2 Hz, 2H), 4.70 (d, J=9.2 Hz, 2H), 1.23 (s, 18H).

$^{13}$C NMR (100 MHz, CDCl$_3$) δ=176.9 (C=O), 118.4 (q, J=318 Hz, CF$_3$), 82.2 (2C, O—CH$_2$—O), 67.0, 65.3 (CH$_2$—P), 38.7 (C(CH$_3$)$_3$), 26.7 (C(CH$_3$)$_3$).

$^{31}$P NMR (162 MHz, CDCl$_3$): δ=12.17.

EXAMPLE 16

General Procedure for Cross-Metathesis with Bis(POM)-Alkenephosphonates

To a CH$_2$Cl$_2$ (25 mL/mmol) solution of N1-crotyl-5-substituted uracil (1 eq.) and bis-(POM)allylphosphonate (1.3 eq.) prepared in example 8, IMes Catalyst (0.05 eq.) was added. This solution was gently refluxed for indicated time under positive pressure of dry argon. After evaporation of all volatiles, the residue was purified by chromatography on silica gel (EtOAc/EP).

The procedure is illustrated in the following scheme

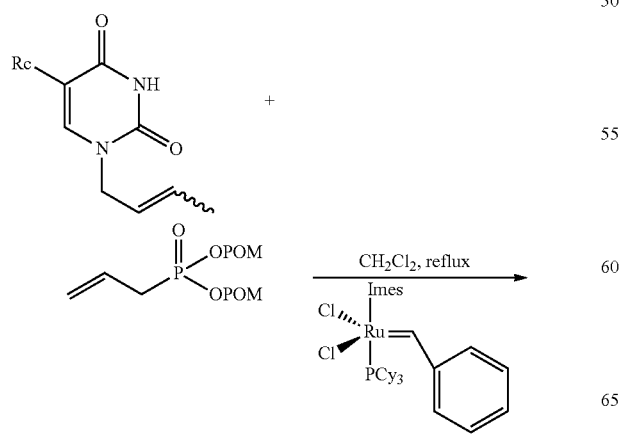

24
-continued

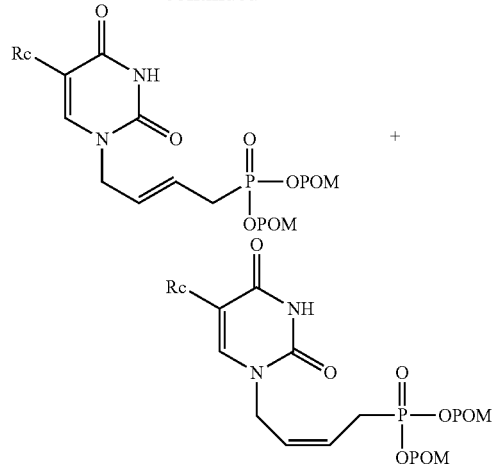

Rc = H, F, Cl, Br, CH$_3$

Compounds of the following examples 17 to 21 are prepared according to this general procedure.

EXAMPLES 17

N$^1$-[(E)-4-bispivaloyloxymethylphosphinyl-2-butenyl]uracil et N$^1$-[(Z)-4-bispivaloyloxymethylphosphinyl-2-butenyl]uracil

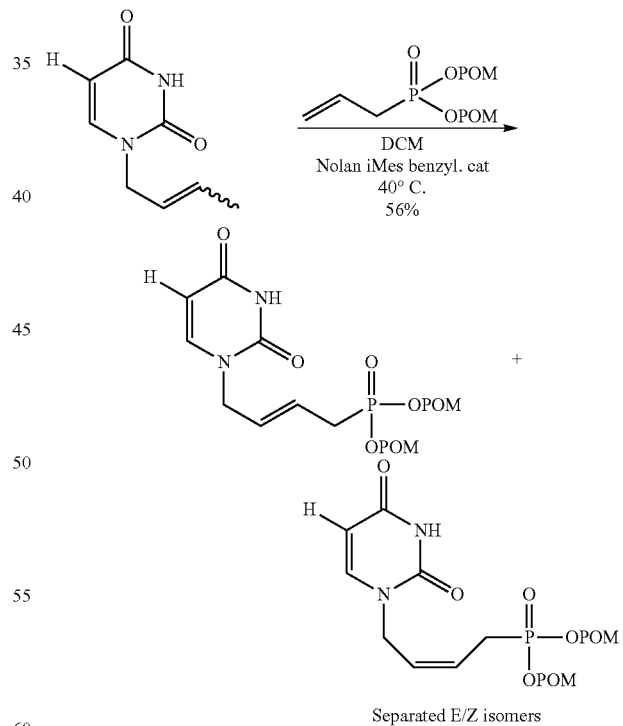

Separated E/Z isomers

N$^1$-[(E)-4-bispivaloyloxymethylphosphinyl-2-butenyl]uracil $^1$H NMR (400 MHz, CDCl$_3$) δ=8.73 (s, 1H, NH), 7.17 (d, J=7.9 Hz, 1H, H$^6$), 5.75-5.61 (m, 7H, O—CH$_2$—O, CH=CH, H⁵), 4.32 (t, J=4.1 Hz, 2H, U—CH₂), 2.72 (dd, J=22.4 Hz, 5.0 Hz, 2H, P—CH₂), 1.23 (s, 18H, tBu).

$^{13}$C NMR (100 MHz, CDCl₃) δ=176.8 (C=O), 163.2 (C=O), 150.5 (C=O), 143.4 (C⁶), 129.5, 129.3 (CH=CH), 124.1, 124.0 (CH=CH), 102.6 (C⁵), 81.6, 81.5 (O—CH₂—O), 49.1, 49.0 (U—CH₂), 38.7 (C(CH₃)₃), 31.5, 30.1 (P—CH₂), 26.8 (C(CH₃)₃).

$^{31}$P NMR (162 MHz, CDCl₃) δ=26.4.

IR ν cm⁻¹: 2977; 1751; 1685; 1459; 1242; 1138; 956; 855.

N¹-[(Z)-4-bispivaloyloxymethylphosphinyl-2-butenyl]uracil $^1$H NMR (400 MHz, CDCl₃) δ=8.32 (s, 1H, NH), 7.47 (d, J=7.9 Hz, 1H, H⁶), 5.77-5.60 (m, 7H, O—CH₂—O, CH=CH, H⁵), 4.44 (t, J=4.7 Hz, 2H, U—CH₂), 2.82 (dd, J=23.4, 6.7 Hz, 2H, P—CH₂), 1.24 (s, 18H, tBu).

$^{13}$C NMR (100 MHz, CDCl₃) δ=177.0 (C=O), 163.2 (C=O), 150.6 (C=O), 144.4 (C⁶), 129.1, 128.9 (CH=CH), 122.1, 122.0 (CH=CH), 102.5 (C⁵), 81.6, 81.5 (O—CH₂—O), 44.8, 44.7 (U—CH₂), 38.8 (C(CH₃)₃), 27.0 and 25.6 (P—CH₂), 26.9 (C(CH₃)₃).

$^{31}$P NMR (162 MHz, CDCl₃): δ=26.6.

EXAMPLE 18

N¹-[(E)-4-bispivaloyloxymethylphosphinyl-2-butenyl]-5-fluorouracil and N¹-[(Z)-4-bispivaloyloxymethylphosphinyl-2-butenyl]-5-fluorouracil

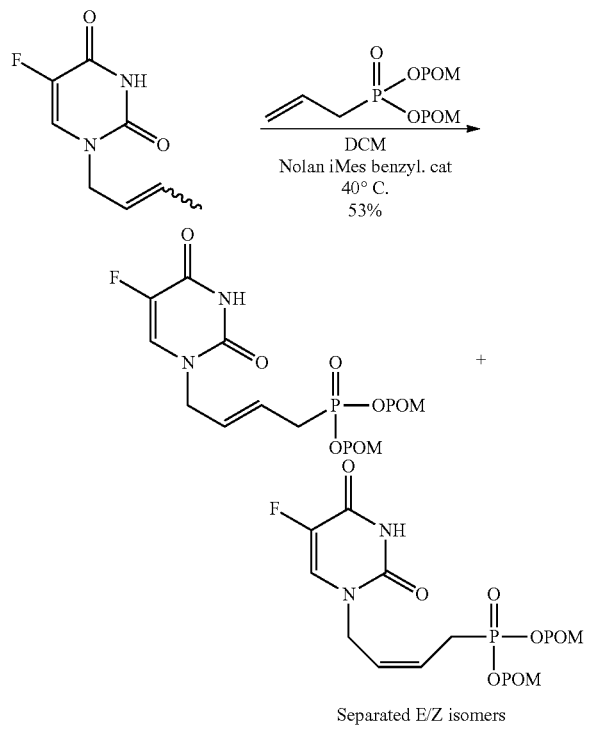

Separated E/Z isomers

N¹-[(E)-4-bispivaloyloxymethylphosphinyl-2-butenyl]-5-fluorouracil $^1$H NMR (400 MHz, CDCl₃): δ=9.58 (s, 1H, NH), 7.28 (d, J=5.5 Hz, 1H, H⁶), 5.77-5.61 (m, 6H, O—CH₂—O, CH=CH), 4.31 (t, J=4.9 Hz, 2H, U—CH₂), 2.72 (dd, J=22.6 Hz, 5.3 Hz, 2H, P—CH₂), 1.22 (s, 18H, tBu).

$^{13}$C NMR (100 MHz, CDCl₃): δ=176.8 (C=O), 157.2, 156.9 (C=O), 149.3 (C=O), 141.7, 139.3 (C⁵), 129.1, 128.9 (CH=CH), 127.7, 127.4 (C⁶), 124.7, 124.6 (CH=CH), 81.6, 81.5 (O—CH₂—O), 49.3 (2C, U—CH₂), 38.6 (C(CH₃)₃), 31.4, 30.0 (P—CH₂), 26.7 (C(CH₃)₃).

$^{31}$P NMR (162 MHz, CDCl₃): δ=26.3.

IR ν cm⁻¹: 2977; 2361; 1752; 1702; 1480; 1238; 1137; 965; 871

N¹-[(Z)-4-bispivaloyloxymethylphosphinyl-2-butenyl]-5-fluorouracil $^1$H NMR (400 MHz, CDCl₃): δ=8.59 (s, 1H, NH), 7.73 (d, J=5.8 Hz, 1H, H⁶), 5.75-5.61 (m, 6H, O—CH₂—O, CH=CH), 4.44 (t, J=4.7 Hz, 2H), 2.80 (dd, J=6.8 Hz, 23.5 Hz, 2H, P—CH₂), 1.23 (s, 18H, tBu).

$^{13}$C NMR (100 MHz, CDCl₃): δ=177.0 (C=O), 157.0, 156.7 (C=O), 149.2 (C=O), 141.7, 139.4 (C⁵), 128.9, 128.7, 128.6 (2C, CH=CH, and C⁶), 122.6, 122.5 (CH=CH), 81.7, 81.6 (O—CH₂—O), 44.9 (2C, U—CH₂), 38.8 (C(CH₃)₃), 26.9 and 25.5 (P—CH₂), 26.8 (C(CH₃)₃).

$^{31}$P NMR (162 MHz, CDCl₃): δ=26.4.

EXAMPLE 19

N¹-[(E)-4-bispivaloyloxymethylphosphinyl-2-butenyl]thymin and N¹-[(Z)-4-bispivaloyloxymethylphosphinyl-2-butenyl]thymin

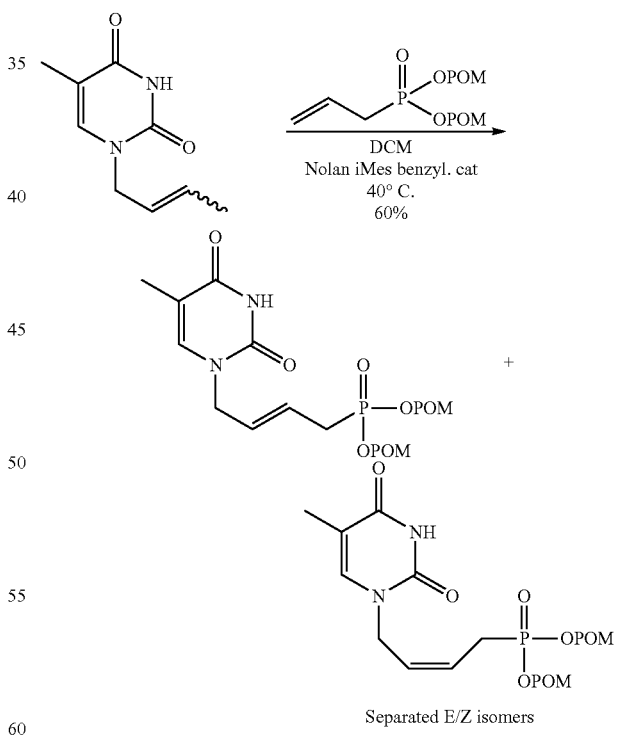

Separated E/Z isomers

N¹-[(E)-4-bispivaloyloxymethylphosphinyl-2-butenyl]thymin $^1$H NMR (400 MHz, CD₃OD): δ=7.37 (d, J=0.9 Hz, 1H, H⁶), 5.85-5.74 (ttd, J=5.1 Hz, 11.2 Hz, 15.4 Hz, 1H, CH=CH), 5.66 (m, 5H, O—CH$_2$—O, CH=CH), 4.32 (t, J=5.2 Hz, 2H, T-CH$_2$), 2.82 (dd, J=22.5 Hz, 7.2 Hz, 2H, P—CH$_2$), 1.87 (s, 3H, CH$_3$—U) 1.23 (s, 18H, tBu).

$^{13}$C NMR (100 MHz, CD$_3$OD): δ=178.1 (C=O), 166.8 (C=O), 152.7 (C=O), 142.4 (C$^6$), 131.8, 131.6 (CH=CH), 123.7, 123.6 (CH=CH), 111.5 (C$^5$), 83.2, 83.1 (O—CH$_2$—O), 49.9 (2C, U—CH$_2$), 39.7 (C(CH$_3$)$_3$), 31.8, 30.4 (P—CH$_2$), 27.2 (C(CH$_3$)$_3$), 12.3 (CH$_3$—U).

$^{31}$P NMR (162 MHz, CD$_3$OD): δ=27.3.

IR ν cm$^{-1}$: 2929; 1678; 1453, 1396; 1196; 986; 751

N$^1$-[(Z)-4-bispivaloyloxymethylphosphinyl-2-butenyl]thymin $^1$H NMR (400 MHz, CD$_3$OD): δ ppm 7.46 (d, J=1.2 Hz, 1H, H$^6$), 5.78-5.60 (m, 7H, O—CH$_2$—O, CH=CH), 4.40 (dd, J=3.8 Hz, 5.5 Hz, 2H), 3.01 (dd, J=23.2, 7.8 Hz, 2H, P—CH$_2$), 1.88 (d, J=1.11 Hz, 3H, CH$_3$—U), 1.24 (d, J=3.16 Hz, 18H, tBu).

$^{13}$C NMR (100 MHz, CD$_3$OD): δ=178.2 (C=O), 166.9 (C=O), 152.9 (C=O), 142.7 (C$^6$), 130.6, 130.4 (CH=CH), 123.0, 122.8 (CH=CH), 111.5 (C$^5$), 83.2, 83.1 (O—CH$_2$—O), 45.6 (U—CH$_2$), 39.8 (C(CH$_3$)$_3$), 27.7 and 26.3 (P—CH$_2$), 27.3 (C(CH$_3$)$_3$), 12.3 (CH$_3$—U).

$^{31}$P NMR (162 MHz, CD$_3$OD): δ=27.6.

EXAMPLE 20

N$^1$-[(E)-4-bispivaloyloxymethylphosphinyl-2-butenyl]-5-chlorouracil and N$^1$-[(Z)-4-bispivaloyloxymethylphosphinyl-2-butenyl]-5-chlorouracil

N$^1$-[(E)-4-bispivaloyloxymethylphosphinyl-2-butenyl]-5-chlorouracil $^1$H NMR (400 MHz, CDCl$_3$): δ=8.73 (s, 1H, NH), 7.42 (s, 1H, H$^6$), 5.80-5.60 (m, 6H, O—CH$_2$—O, CH=CH), 4.33 (t, J=4.5 Hz, 2H, U—CH$_2$), 2.72 (dd, J=5.7 Hz, 22.6 Hz, 2H, P—CH$_2$), 1.23 (s, 18H, tBu).

$^{13}$C NMR (100 MHz, CDCl$_3$): δ=176.8 (C=O), 158.8 (C=O), 149.4 (C=O), 140.3 (C$^6$), 129.0, 128.8 (CH=CH), 125.0, 124.9 (CH=CH), 109.0 (C$^5$), 81.6 (2C, O—CH$_2$—O), 49.5 (2C, U—CH$_2$), 38.7 (C(CH$_3$)$_3$), 31.5, 30.1 (P—CH$_2$), 26.8 (C(CH$_3$)$_3$).

$^{31}$P NMR (162 MHz, CDCl$_3$): δ=26.1.

IR ν cm$^{-1}$: 2976; 1752; 1692; 1452; 1236; 1135; 963; 853.

N$^1$-[(Z)-4-bispivaloyloxymethylphosphinyl-2-butenyl]-5-chlorouracil $^1$H NMR (400 MHz, CDCl$_3$): δ=8.48 (s, 1H, NH), 7.79 (s, 1H, H$^6$), 5.74-5.62 (m, 6H, O—CH$_2$—O, CH=CH), 4.47 (t, J=4.63 Hz, 2H, U—CH$_2$), 2.82 (dd, J=23.5 Hz, 6.9 Hz, 2H, P—CH$_2$), 1.24 (s, 18H).

$^{13}$C NMR (100 MHz, CDCl$_3$): δ=177.0 (C=O), 158.9 (C=O), 149.7 (C=O), 141.3 (C$^6$), 128.6, 128.4 (CH=CH), 122.7, 122.6 (C$^6$), 108.9 (C$^5$), 81.7, 81.6 (O—CH$_2$—O), 45.1 (2C, U—CH$_2$), 38.8 (C(CH$_3$)$_3$), 27.0 and 25.6 (P—CH$_2$), 26.8 (C(CH$_3$)$_3$).

EXAMPLE 21

N$^1$-[(E)-4-bispivaloyloxymethylphosphinyl-2-butenyl]-5-bromouracil and N$^1$-[(Z)-4-bispivaloyloxymethylphosphinyl-2-butenyl]-5-bromouracil

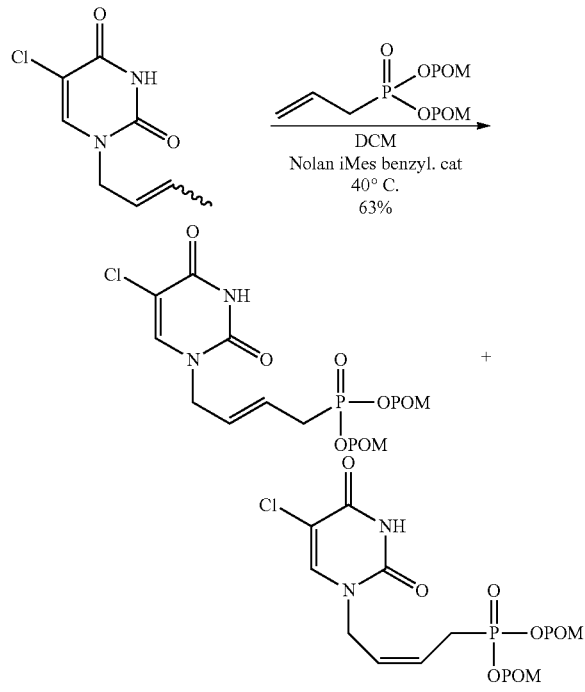

Separated E/Z isomers

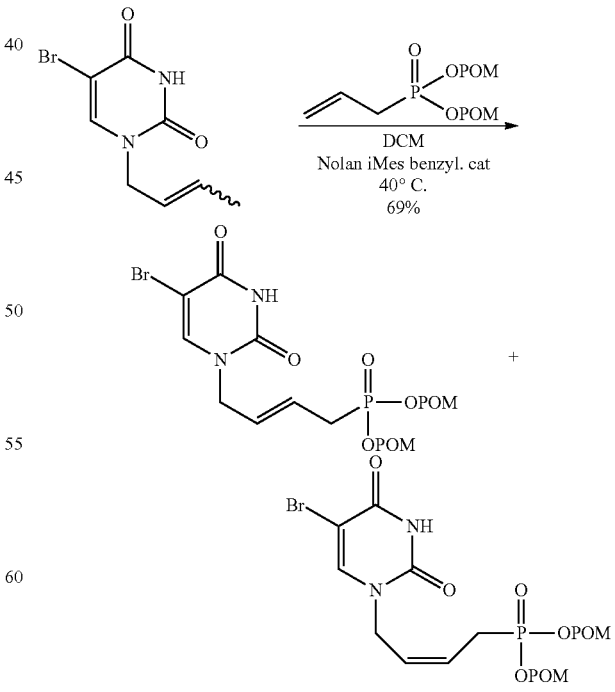

Separated E/Z isomers

$N^1$-[(E)-4-bispivaloyloxymethylphosphinyl-2-butenyl]-5-bromouracil $^1$H NMR (400 MHz, CD$_3$OD): δ=7.98 (s, 1H, H$^6$), 5.85-5.76 (m, 1H, CH=CH), 5.75-5.62 (m, 5H, O—CH$_2$—O, CH=CH), 4.36 (t, J=5.1 Hz, 2H, U—CH$_2$), 2.82 (dd, J=22.5 Hz, 6.9 Hz, 2H, P—CH$_2$), 1.23 (s, 18H, tBu).

$^{13}$C NMR (100 MHz, CD$_3$OD): δ=178.1 (C=O), 162.1 (C=O), 152.0 (C=O), 146.2 (C$^6$), 131.4, 131.3 (CH=CH), 124.5, 124.4 (CH=CH), 96.8 (C$^5$), 83.3, 83.2 (O—CH$_2$—O), 50.6, 50.5 (U—CH$_2$), 39.8 (C(CH$_3$)$_3$), 31.9, 30.5 (P—CH$_2$), 27.2 (C(CH$_3$)$_3$).

$^{31}$P NMR (162 MHz, CD$_3$OD): δ=27.1.

IR ν cm$^{-1}$: 2976; 2361; 1751; 1693; 1441; 1235; 1137; 965; 854, 768.

$N^1$-[(Z)-4-bispivaloyloxymethylphosphinyl-2-butenyl]-5-bromouracil $^1$H NMR (400 MHz, CD$_3$OD): δ=8.06 (s, 1H, H$^6$), 5.70-5.52 (m, 6H, O—CH$_2$—O, CH=CH), 4.45 (dd, J=6.8 Hz, 3.7 Hz, 2H), 3.01 (dd, J=23.4, 7.8 Hz, 2H), 1.24 (s, 18H).

$^{13}$C NMR (100 MHz, CD$_3$OD): δ=178.2 (C=O), 162.2 (C=O), 152.1 (C=O), 146.3 (C$^6$), 130.1, 129.9 (CH=CH), 123.5, 123.4 (CH=CH), 96.7 (C$^5$), 83.2, 83.1 (O—CH$_2$—O), 46.2 (2C, U—CH$_2$), 39.8 (C(CH$_3$)$_3$), 27.7 and 26.3 (P—CH$_2$), 27.3 (C(CH$_3$)$_3$).

$^{31}$P NMR (100 MHz, CD$_3$OD): δ=27.5.

EXAMPLE 22

General Procedure for Cross-Metathesis with Bis(POC)-Alkenephosphonates

To a CH$_2$Cl$_2$ (25 mL/mmol) solution of N1-crotyl-5-substituted uracil (1 eq.) and bis-(POC) allylphosphonate (1.3 eq.) prepared according to example 9, IPr Catalyst (0.05 eq.) was added. This solution was stirred at room temperature for indicated time under positive pressure of dry argon. After evaporation of all volatiles, the residue was purified by chromatography on silica gel (EtOAc/EP).

The procedure is illustrated in the following scheme

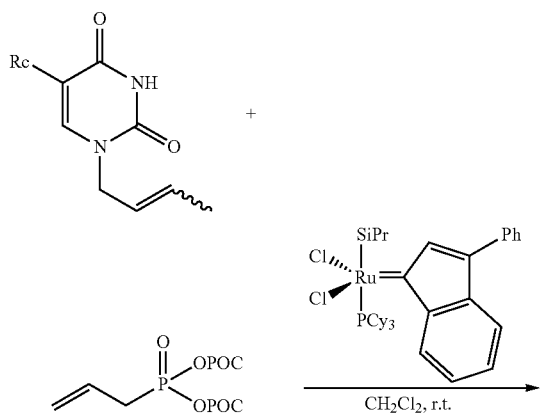

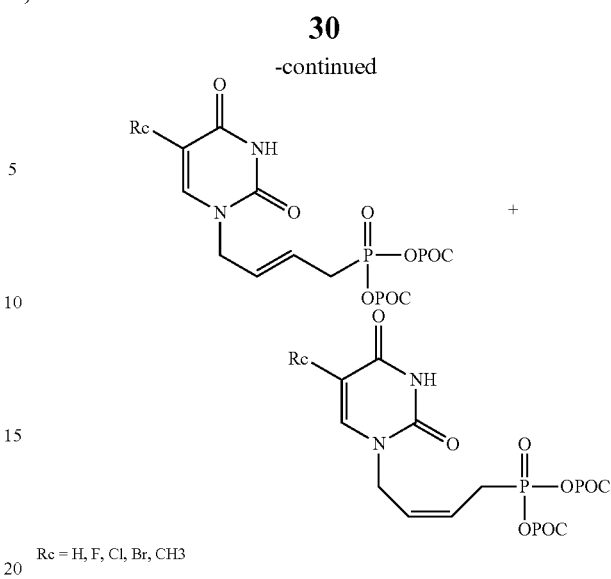

Rc = H, F, Cl, Br, CH3

Compounds of the following examples 23 to 27 are prepared according this general procedure.

EXAMPLE 23

$N^1$-[(E)-4-bisisopropyloxycarbonyloxymethylphosphinyl-2-butenyl]uracil and $N^1$-[(Z)-4-bisisopropyloxycarbonyloxymethylphosphinyl-2-butenyl]uracil

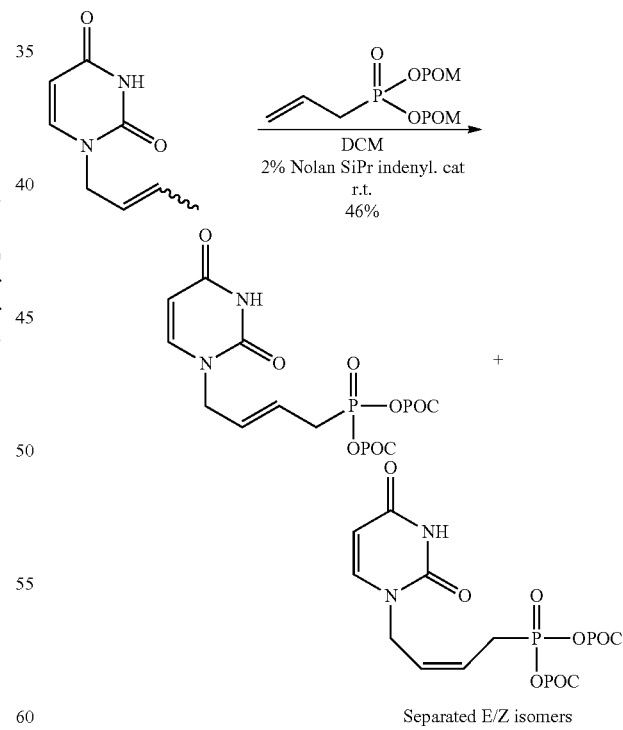

Separated E/Z isomers

$N^1$-[(E)-4-bisisopropyloxycarbonyloxymethylphosphinyl-2-butenyl]uracil $^1$H NMR (400 MHz, CDCl$_3$) δ=8.94 (s, 1H, NH), 7.19 (d, J=7.9 Hz, 1H, H$^6$), 5.74-5.61 (m, 7H, O—CH$_2$—O, CH=CH, H⁵), 4.92 (sept., J=6.2 Hz, 2H, CH(CH₃)₂), 4.33 (t, J=4.4 Hz, 2H, U—CH₂), 2.76 (dd, J=22.8, 5.6 Hz, 2H, P—CH₂), 1.32 (d, J=6.3 Hz, 12H, CH(CH₃)₂). $^{13}$C NMR (100 MHz, CDCl₃) δ=163.3 (C=O), 153.0 (C=O), 150.6 (C=O), 143.4 (C⁶), 129.7, 129.6 (CH=CH), 123.8, 123.7 (CH=CH), 102.5 (C⁵), 84.1, 84.0 (O—CH₂—O), 73.4 (CH(CH₃)₂), 48.9 (2C, U—CH₂), 31.3, 29.9 (P—CH₂), 21.6 (CH(CH₃)₂).
$^{31}$P NMR (162 MHz, CDCl₃): δ=26.8.
IR ν cm⁻¹: 2896; 1755; 1679; 1457; 1257; 1152; 1100; 981; 949; 830.

N¹-[(Z)-4-bisisopropyloxycarbonyloxym-ethylphosphinyl-2-butenyl]uracil $^{1}$H NMR (400 MHz, CDCl₃): δ=8.36 (s, 1H, NH), 7.30 (d, J=5.6 Hz, 1H, H⁶), 5.80-5.60 (m, 7H, O—CH₂—O, CH=CH, H⁵), 4.93 (sept, J=6.3 Hz, 2H, CH(CH₃)₂), 4.32 (t, J=4.17 Hz, 2H, U—CH₂), 2.77 (dd, J=22.9, 5.5 Hz, 2H, P—CH₂), 1.33 (d, J=6.3 Hz, 12H, CH(CH₃)₂).
$^{13}$C NMR (100 MHz, CDCl₃): δ=163.5 (C=O), 153.1 (C=O), 148.8 (C=O), 141.7 (C⁶), 129.2, 129.1 (CH=CH), 127.8, 127.5 (CH=CH), 124.6, 124.5 (CH=CH), 84.2, 84.1 (O—CH₂—O), 73. (CH(CH₃)₂), 49.3 (2C, U—CH₂), 31.3, 29.9 (P—CH₂), 21.6 (2C, CH(CH₃)₂).
$^{31}$P NMR (162 MHz, CDCl₃): δ=26.6.

EXAMPLE 24

N¹-[(E)-4-bisisopropyloxycarbonyloxym-ethylphosphinyl-2-butenyl]thymin and N¹-[(Z)-4-bisisopropyloxycarbonyloxymethylphosphinyl-2-butenyl]thymin

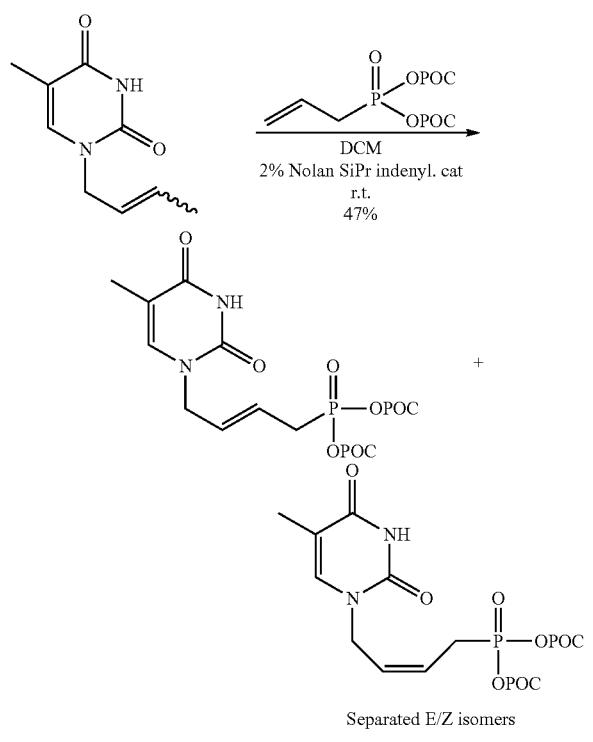

Separated E/Z isomers

N¹-[(E)-4-bisisopropyloxycarbonyloxym-ethylphosphinyl-2-butenyl]thymin $^{1}$H NMR (400 MHz, CDCl₃): δ=9.06 (s, 1H, NH), 7.00 (d, J=1.0 Hz, 1H, H⁶), 5.76-5.60 (m, 6H, O—CH₂—O, CH=CH), 4.91 (sept., J=6.3 Hz, 2H, CH(CH₃)₂), 4.30 (t, J=4.6 Hz, 2H, U—CH₂), 2.74 (dd, J=22.6 Hz, 5.9 Hz, 2H, P—CH₂), 1.90 (d, J=0.7 Hz, 3H, CH₃—U), 1.31 (d, J=6.3 Hz, 12H, CH(CH₃)₂).
$^{13}$C NMR (100 MHz, CDCl₃): δ=164.0 (C=O), 153.0 (C=O), 150.7 (C=O), 139.4 (C⁶), 130.1, 130.0 (CH=CH), 123.3, 123.1 (CH=CH), 111.0 (C⁵), 84.1, 84.0 (O—CH₂—O), 73.3 (CH(CH₃)₂), 48.7 (2C, U—CH₂), 31.3, 29.9 (P—CH₂), 21.5 (2C, CH(CH₃)₂), 12.2 (CH₃—U).
$^{31}$P NMR (162 MHz, CDCl₃): δ=27.0.
IR ν cm⁻¹: 2985; 1756; 1679; 1467; 1257; 1152; 1101; 982; 950; 831; 788.

N¹-[(Z)-4-bisisopropyloxycarbonyloxym-ethylphosphinyl-2-butenyl]thymin $^{1}$H NMR (400 MHz, CDCl₃): δ=8.13 (s, 1H, NH), 7.23 (d, J=1.2 Hz, 1H, H⁶), 5.76-5.61 (m, 6H, O—CH₂—O, CH=CH), 5.00-4.87 (sept, J=6.3 Hz, 2H, CH(CH₃)₂), 4.41 (t, J=4.6 Hz, 2H, U—CH₂), 2.88 (dd, J=23.2, 6.3 Hz, 2H, P—CH₂), 1.92 (s, 3H, CH₃—U), 1.33 (d, J=6.3 Hz, 12H, CH(CH₃)₂).
$^{13}$C NMR (100 MHz, CDCl₃): δ=163.7 (C=O), 153.1 (C=O), 150.6 (C=O), 140.1 (C⁶), 129.4, 129.3 (CH=CH), 121.6, 121.5 (CH=CH), 110.9 (C⁵), 84.1 (2C, O—CH₂—O), 73.4 (CH(CH₃)₂), 44.4 (2C, U—CH₂), 27.0, 25.6 (P—CH₂), 21.6 (CH(CH₃)₂), 12.2 (CH₃—U).
$^{31}$P NMR (162 MHz, CDCl₃): δ=26.8.

EXAMPLE 25

N¹-[(E)-4-bisisopropyloxycarbonyloxym-ethylphosphinyl-2-butenyl]-5-fluorouracil and N¹-[(Z)-4-bisisopropyloxycarbonyloxym-ethylphosphinyl-2-butenyl]-5-fluorouracil

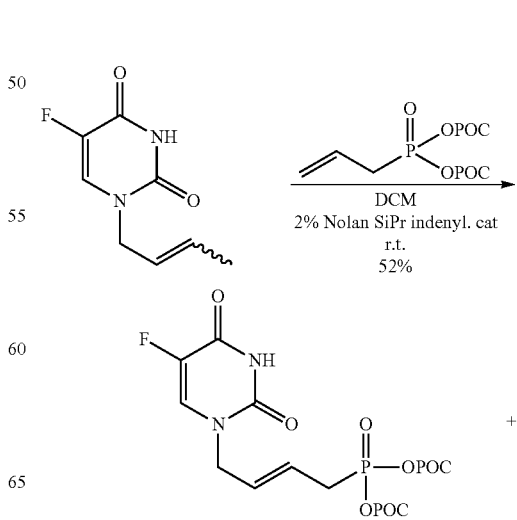

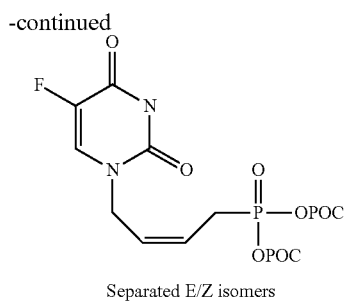

Separated E/Z isomers

N¹-[(E)-4-bisisopropyloxycarbonyloxym-ethylphosphinyl-2-butenyl]-5-fluorouracil $^1$H NMR (400 MHz, CDCl$_3$): δ=9.44 (s, 1H, NH), 7.31 (d, J=5.5 Hz, 1H, H$^6$), 5.78-5.61 (m, 6H, O—CH$_2$—O, CH=CH), 4.92 (sept, J=6.3 Hz, 2H, CH(CH$_3$)$_2$), 4.32 (t, J=4.6 Hz, 2H, U—CH$_2$), 2.77 (dd, J=23.0, 5.1 Hz, 2H, P—CH$_2$), 1.31 (d, J=6.3 Hz, 12H, CH(CH$_3$)$_2$).

$^{13}$C NMR (100 MHz, CDCl$_3$): δ=157.2, 156.9 (C=O), 153.1 (C=O), 149.3 (C=O), 141.8, 139.4 (C$^5$), 129.4, 129.2 (CH=CH), 127.8, 127.5 (C$^6$), 124.4, 124.3 (CH=CH), 84.2 (2C, O—CH$_2$—O), 73.5 (CH(CH$_3$)$_2$), 49.3, 49.2 (U—CH$_2$), 31.3, 29.9 (P—CH$_2$), 21.6 (2C, CH(CH$_3$)$_2$).

$^{31}$P NMR (162 MHz, CDCl$_3$): δ=26.8.

IR ν cm$^{-1}$: 2987; 1756; 1694; 1468; 1259; 1152; 1101; 981; 949; 870; 831; 787.

N¹-[(Z)-4-bisisopropyloxycarbonyloxym-ethylphosphinyl-2-butenyl]-5-fluorouracil $^1$H NMR (400 MHz, CDCl$_3$): δ=8.40 (s, 1H, NH), 7.70 (d, J=5.8 Hz, 1H, H$^6$), 5.78-5.61 (m, 6H, O—CH$_2$—O, CH=CH), 4.94 (sept, J=6.3 Hz, 2H, CH(CH$_3$)$_2$), 4.45 (t, J=4.8 Hz, 2H, U—CH$_2$), 2.93-2.79 (dd, J=23.7, 6.8 Hz, 2H, P—CH$_2$), 1.33 (d, J=6.3 Hz, 12H, CH(CH$_3$)$_2$).

$^{13}$C NMR (100 MHz, CDCl$_3$): δ=157.2, 156.9 (C=O), 153.178 (C=O), 149.2 (C=O), 128.9, 128.7 (CH=CH), 122.4, 122.2 (CH=CH), 84.3 (2C, O—CH$_2$—O), 73.5 (CH(CH$_3$)$_2$), 44.9 (2C, U—CH$_2$), 26.9, 25.5 (P—CH$_2$), 21.6 (CH(CH$_3$)$_2$).

$^{31}$P NMR (162 MHz, CDCl$_3$): δ=26.6.

EXAMPLE 26

N¹-[(E)-4-bisisopropyloxycarbonyloxym-ethylphosphinyl-2-butenyl]-5-chlorouracil and N¹-[(Z)-4-bisisopropyloxycarbonyloxym-ethylphosphinyl-2-butenyl]-5-chlorouracil

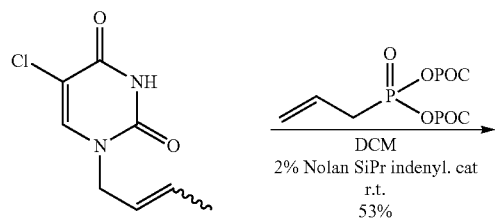

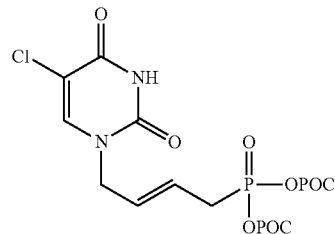

Separated E/Z isomers

N¹-[(E)-4-bisisopropyloxycarbonyloxym-ethylphosphinyl-2-butenyl]-5-chlorouracil $^1$H NMR (400 MHz, CDCl$_3$): δ=9.31 (s, 1H, NH), 7.45 (s, 1H, H$^6$), 5.76-5.61 (m, 6H, O—CH$_2$—O, CH=CH), 4.92 (sept., J=6.3 Hz, 2H, CH(CH$_3$)$_2$), 4.34 (t, J=4.2 Hz, 2H, U—CH$_2$), 2.77 (dd, J=22.8, 5.6 Hz, 2H, P—CH$_2$), 1.31 (d, J=6.3 Hz, 12H, CH(CH$_3$)$_2$).

$^{13}$C NMR (100 MHz, CDCl$_3$): δ=159.1 (C=O), 153.0 (C=O), 149.7 (C=O), 140.4 (C$^6$), 129.3, 129.2 (CH=CH), 124.5, 124.4 (CH=CH), 109.0 (C$^5$), 84.2, 84.1 (O—CH$_2$—O), 73.4 (CH(CH$_3$)$_2$), 49.4 (2C, U—CH$_2$), 31.3, 29.9 (P—CH$_2$), 21.6, 21.5 (CH(CH$_3$)$_2$).

$^{31}$P NMR (162 MHz, CDCl$_3$): δ=26.7.

IR ν cm$^{-1}$: 2986; 1756; 1686; 1451; 1348; 1258; 1152; 1186; 981; 949; 903; 869; 831; 787.

N¹-[(Z)-4-bisisopropyloxycarbonyloxym-ethylphosphinyl-2-butenyl]-5-chlorouracil $^1$H NMR (400 MHz, CDCl$_3$): δ=8.79 (s, 1H, NH), 7.76 (s, 1H, H$^6$), 5.74-5.61 (m, 6H, O—CH$_2$—O, CH=CH), 4.93 (sept., J=6.3 Hz, 2H, CH(CH$_3$)$_2$), 4.47 (t, J=4.7 Hz, 2H, U—CH$_2$), 2.87 (dd, J=23.6, 6.7 Hz, 2H, P—CH$_2$), 1.32 (d, J=6.3 Hz, 12H, CH(CH$_3$)$_2$).

$^{13}$C NMR (100 MHz, CDCl$_3$): δ=159.0 (C=O), 153.1 (C=O), 149.7 (C=O), 141.3 (C$^6$), 128.7, 128.6 (CH=CH), 122.4, 122.3 (CH=CH), 108.9 (C$^5$), 84.2, 84.1 (O—CH$_2$—O), 73.5 (CH(CH$_3$)$_2$), 45.1, 45.0 (U—CH$_2$), 26.9, 25.5 (P—CH$_2$), 21.6 (CH(CH$_3$)$_2$).

$^{31}$P NMR (162 MHz, CDCl$_3$): δ=26.6.

EXAMPLE 27

N¹-[(E)-4-bisisopropyloxycarbonyloxym-
ethylphosphinyl-2-butenyl]-5-bromorouracil and
N¹-[(Z)-4-bisisopropyloxycarbonyloxym-
ethylphosphinyl-2-butenyl]-5-bromorouracil

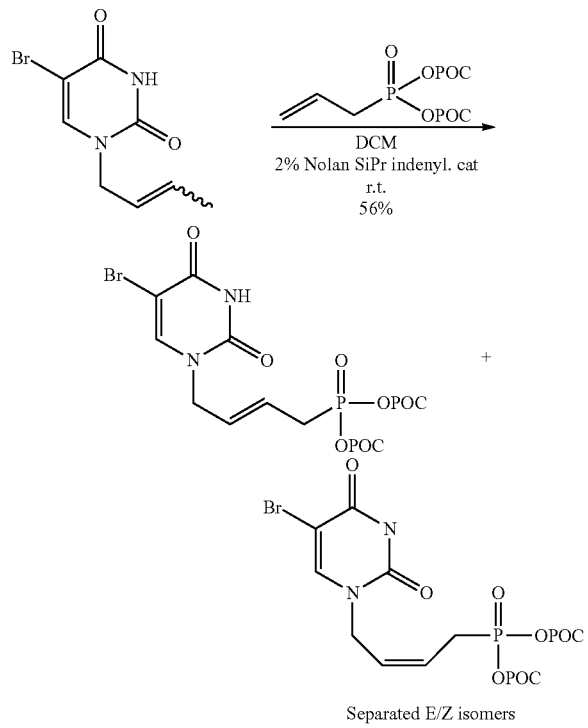

Separated E/Z isomers

N¹-[(E)-4-bisisopropyloxycarbonyloxym-
ethylphosphinyl-2-butenyl]-5-bromorouracil $^{1}$H NMR (400 MHz, CDCl$_3$): δ=9.45 (s, 1H, NH), 7.51 (s, 1H, H$^6$), 5.75-5.55 (m, 6H, O—CH$_2$—O, CH=CH), 4.87 (sept., J=6.3 Hz, 2H, CH(CH$_3$)$_2$), 4.29 (t, J=4.1 Hz, 2H, U—CH$_2$), 2.72 (dd, J=22.4, 5.2 Hz, 2H, P—CH$_2$), 1.26 (d, J=6.27 Hz, 12H, CH(CH$_3$)$_2$).

$^{13}$C NMR (100 MHz, CDCl$_3$): δ=159.3 (C=O), 153.1 (C=O), 150.0 (C=O), 143.0 (C$^6$), 129.4, 129.3 (CH=CH), 124.5, 124.4 (CH=CH), 96.7 (C$^5$), 84.2 (2C, O—CH$_2$—O), 73.4 (CH(CH$_3$)$_2$), 49.4 (2C, U—CH$_2$), 31.3, 29.9 (P—CH$_2$), 21.6 (2C, CH(CH$_3$)$_2$).

$^{31}$P NMR (162 MHz, CDCl$_3$): δ=26.8.

IR ν cm$^{-1}$: 2986; 1756; 1691; 1442; 1347; 1260; 1153; 1186; 1029; 983; 951; 871; 832; 789.

N¹-[(Z)-4-bisisopropyloxycarbonyloxym-
ethylphosphinyl-2-butenyl]-5-bromorouracil $^{1}$H NMR (400 MHz, CDCl$_3$): δ=8.40 (s, 1H, NH), 7.86 (s, 1H, H$^6$), 5.76-5.61 (m, 6H, O—CH$_2$—O, CH=CH), 4.94 (sept, J=6.3 Hz, 2H, CH(CH$_3$)$_2$), 4.47 (t, J=4.6 Hz, 2H, U—CH$_2$), 2.87 (dd, J=23.6, 6.8 Hz, 2H, P—CH$_2$), 1.33 (d, J=6.2 Hz, 12H, CH(CH$_3$)$_2$).

$^{13}$C NMR (100 MHz, CDCl$_3$): δ=159.0 (C=O), 153.2 (C=O), 149.9 (C=O), 143.9 (C$^6$), 128.7, 128.6 (CH=CH), 122.5, 122.4 (CH=CH), 96.5 (C$^5$), 84.3, 84.2 (O—CH$_2$—O), 73.5 (CH(CH$_3$)$_2$), 45.1 (2C, U—CH$_2$), 27.0, 25.6 (P—CH$_2$), 21.6 (2C, CH(CH$_3$)$_2$).

$^{31}$P NMR (162 MHz, CDCl$_3$): δ=26.6.

EXAMPLE 28

General Procedure for Cross-Metathesis with HDP-POC Allylphosphonate

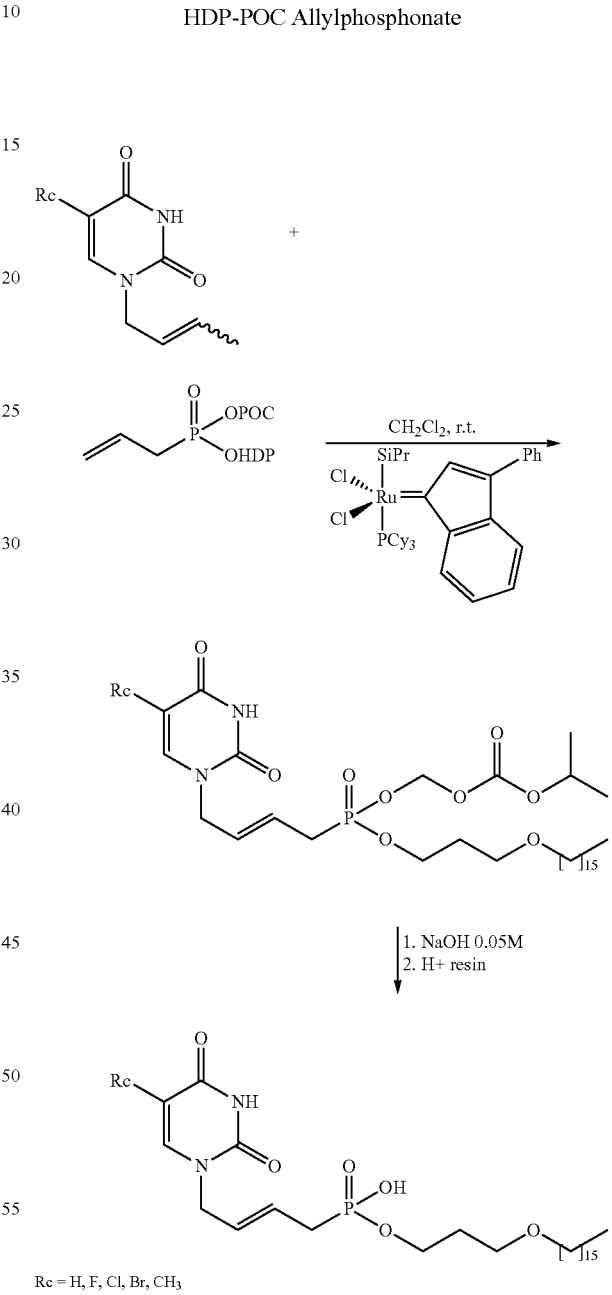

Rc = H, F, Cl, Br, CH$_3$

28.1. General Procedure for Cross-Metathesis with IPr NHC Catalysts

To a CH$_2$Cl$_2$ (25 mL/mmol) solution of N1-crotyl-5-substituted uracil (1 eq.) and HDP-POC-allylphosphonate (1.3 eq.) prepared according to example 11, IPr Catalyst (0.05 eq.) was added. This solution was stirred a room temperature for indicated time under positive pressure of dry argon. After evaporation of all volatiles, the residue was purified by chromatography on silica gel (EtOAc/EP).

28.2. General Procedure for Deprotection of POC:

To N$^1$-[(E)-O-hexadecyloxypropyl isopropyloxycarbonyloxymethyl-phosphinyl-2-butenyl]-5-substituted uracil prepared in example 28.1 was added a 0.1M solution (1 ml) of sodium hydroxide in demineralized water. This solution was stirred a room temperature for 4 h. The basic solution is neutralized with acidic DOWEX resin 50w8 and washed two times with DCM (1 ml). Pure product is directly obtain after evaporation of all volatiles, Compounds of examples 29 to 38 are synthesized according to said general procedure

EXAMPLE 29

N$^1$-[(E)-O-hexadecyloxypropyl isopropyloxycarbonyloxymethyl-phosphinyl-2-butenyl]uracil

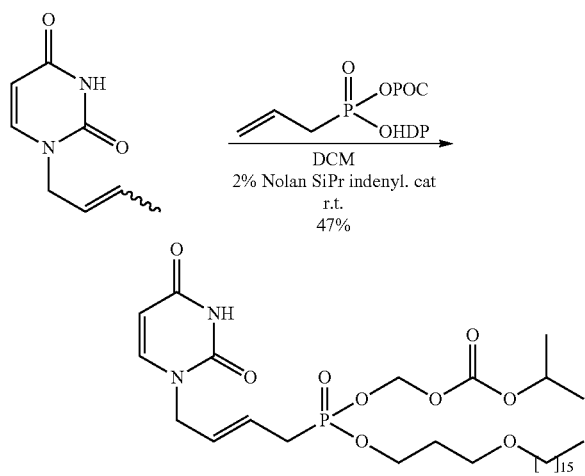

$^1$H NMR (400 MHz, CDCl$_3$): δ=8.93 (s, 1H, NH), 7.18 (d, 1H, J=7.9 Hz, H$^6$), 5.73-5.68 (m, 3H, CH=CH, H$^5$), 5.63 (td, J=13.9, 5.3 Hz, 2H, O—CH$_2$—O) 4.92 (sept., J=6.3 Hz, 2H, CH(CH$_3$)$_2$), 4.39-4.26 (m, 2H, U—CH$_2$), 4.25-4.08 (m, 2H, P—O—CH$_2$—CH$_2$—CH$_2$—O), 3.46 (t, J=6.1 Hz, 2H, P—O—CH$_2$—CH$_2$—CH$_2$—O), 3.38 (t, J=6.7 Hz, 2H, O—CH$_2$—CH$_2$—(CH$_2$)$_{13}$—CH$_3$), 2.69 (dd, J=22.0, 5.2 Hz, 2H, CH$_2$—P), 1.91 (p, J=6.3 Hz, 2H, P—O—CH$_2$—CH$_2$—CH$_2$—O), 1.54 (p, J=6.9 Hz, 2H, O—CH$_2$—CH$_2$—(CH$_2$)$_{13}$—CH$_3$), 1.34-1.20 (m, 32H, O—CH$_2$—CH$_2$—(CH$_2$)$_{13}$—CH$_3$, CH(CH$_3$)$_2$), 0.87 (t, J=6.8 Hz, 3H, O—CH$_2$—CH$_2$—(CH$_2$)$_{13}$—CH$_3$).

$^{13}$C NMR (100 MHz, CDCl$_3$): δ=163.3 (C=O), 153.1 (C=O), 150.5 (C=O), 143.4 (C$^6$), 129.0, 128.9 (CH=CH), 124.7, 124.6 (CH=CH), 102.5 (C$^5$), 84.4, 84.3 (O—CH$_2$—O), 73.2 (CH(CH$_3$)$_2$), 71.2 (O—CH$_2$—CH$_2$—(CH$_2$)$_{13}$—CH$_3$), 66.3 (P—O—CH$_2$—CH$_2$—CH$_2$—O), 63.5 (2C, P—O—CH$_2$—CH$_2$—CH$_2$—O), 49.0 (2C, U—CH$_2$), 31.8, 31.1, 30.7, 30.6, 29.7, 29.6 (3C), 29.5, 29.4, 29.3, 26.1, 22.6, 21.6 (CH$_2$—P, CH(CH$_3$)$_2$, P—O—CH$_2$—CH$_2$—CH$_2$—O, O—CH$_2$—CH$_2$—(CH$_2$)$_{13}$—CH$_3$), 14.0 (O—CH$_2$—CH$_2$—(CH$_2$)$_{13}$—CH$_3$).

$^{31}$P NMR (162 MHz, CDCl$_3$): δ=26.7.

EXAMPLE 30

N$^1$-[(E)-O-hexadecyloxypropyl isopropyloxycarbonyloxymethyl-phosphinyl-2-butenyl]-5-chlorouracil

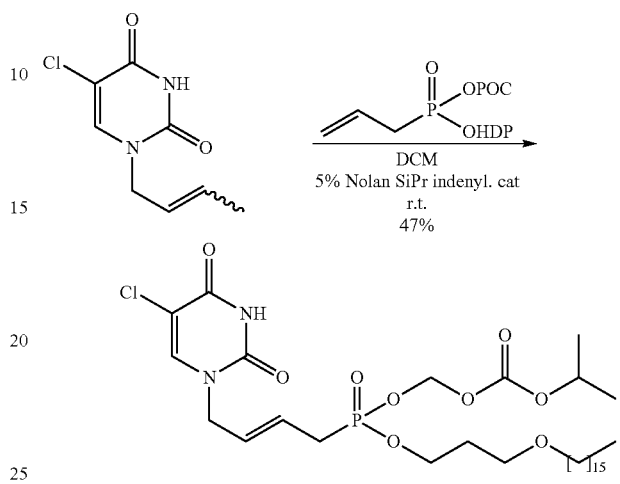

$^1$H NMR (400 MHz, CDCl$_3$): δ=9.44 (s, 1H, NH), 7.43 (s, 1H, H$^6$), 5.80-5.60 (m, 4H, CH=CH, O—CH$_2$—O), 4.91 (sept., J=6.3 Hz, 2H, CH(CH$_3$)$_2$), 4.38-4.29 (m, 2H, U—CH$_2$), 4.23-4.10 (m, 2H, P—O—CH$_2$—CH$_2$—CH$_2$—O), 3.46 (t, J=6.1 Hz, 2H, P—O—CH$_2$—CH$_2$—CH$_2$—O), 3.37 (t, J=6.7 Hz, 2H, O—CH$_2$—CH$_2$—(CH$_2$)$_{13}$—CH$_3$), 2.71 (dd, J=22.5, 6.6 Hz, 2H, CH$_2$—P), 1.91 (p, J=6.3 Hz, 2H, P—O—CH$_2$—CH$_2$—CH$_2$—O), 1.53 (p, J=6.9 Hz, 2H, O—CH$_2$—CH$_2$—(CH$_2$)$_{13}$—CH$_3$), 1.32-1.22 (m, 32H, O—CH$_2$—CH$_2$—(CH$_2$)$_{13}$—CH$_3$, CH(CH$_3$)$_2$), 0.86 (t, J=6.8 Hz, 3H, O—CH$_2$—CH$_2$—(CH$_2$)$_{13}$—CH$_3$).

$^{13}$C NMR (100 MHz, CDCl$_3$): δ=159.1 (C=O), 153.2 (C=O), 149.8 (C=O), 140.3 (C$^6$), 128.6, 128.5 (CH=CH), 125.6, 125.5 (CH=CH), 109.0 (C$^5$), 84.5, 84.4 (O—CH$_2$—O), 73.2 (CH(CH$_3$)$_2$), 71.2 (O—CH$_2$—CH$_2$—(CH$_2$)$_{13}$—CH$_3$), 66.4 (P—O—CH$_2$—CH$_2$—CH$_2$—O), 63.7, 63.6 (P—O—CH$_2$—CH$_2$—CH$_2$—O), 49.5, 49.4 (U—CH$_2$), 31.9, 31.1, 30.7, 30.6, 29.7 (2C), 29.6 (2C), 29.5, 29.3, 26.1, 22.6, 21.6 (2C)(CH$_2$—P, CH(CH$_3$)$_2$, P—O—CH$_2$—CH$_2$—CH$_2$—O, O—CH$_2$—CH$_2$—(CH$_2$)$_{13}$—CH$_3$), 14.1 (O—CH$_2$—CH$_2$—(CH$_2$)$_{13}$—CH$_3$).

$^{31}$P NMR (162 MHz, CDCl$_3$): δ=26.6.

EXAMPLE 31

N$^1$-[(E)-O-hexadecyloxypropyl isopropyloxycarbonyloxymethyl-phosphinyl-2-butenyl]-5-bromouracil

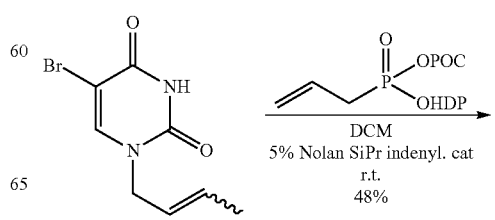

-continued

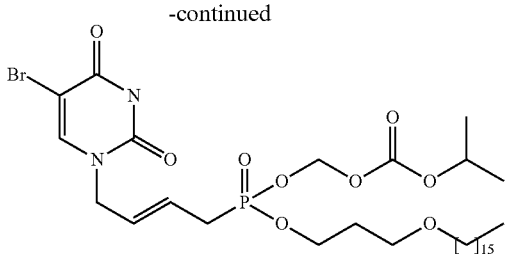

¹H NMR (400 MHz, CDCl₃): δ=8.58 (s, 1H, NH), 7.54 (s, 1H, H⁶), 5.84-5.59 (m, 4H, CH=CH, O—CH₂—O), 4.93 (sept., J=6.3 Hz, 2H, CH(CH₃)₂), 4.40-4.30 (m, 2H, U—CH₂), 4.26-4.08 (m, 2H, P—O—CH₂—CH₂—CH₂—O), 3.47 (t, J=6.1 Hz, 2H, P—O—CH₂—CH₂—CH₂—O), 3.39 (t, J=6.7 Hz, 2H, O—CH₂—CH₂—(CH₂)₁₃—CH₃), 2.72 (dd, J=22.5, 6.8 Hz, 2H, CH₂—P), 1.92 (p, J=6.3 Hz, 2H, P—O—CH₂—CH₂—CH₂—O), 1.55 (p, J=6.9 Hz, 2H, O—CH₂—CH₂—(CH₂)₁₃—CH₃), 1.34-1.22 (m, 32H, O—CH₂—CH₂—(CH₂)₁₃—CH₃, CH(CH₃)₂), 0.88 (t, J=6.8 Hz, 3H, O—CH₂—CH₂—(CH₂)₁₃—CH₃).

¹³C NMR (100 MHz, CDCl₃): δ=158.9 (C=O), 153.2 (C=O), 149.7 (C=O), 142.9 (C⁶), 128.6, 128.4 (CH=CH), 125.8, 125.7 (CH=CH), 96.7 (C⁵), 84.5 (2C, O—CH₂—O), 73.3 (CH(CH₃)₂), 71.2 (O—CH₂—CH₂—(CH₂)₁₃—CH₃), 66.4 (P—O—CH₂—CH₂—CH₂—O), 63.7, 63.6 (P—O—CH₂—CH₂—CH₂—O), 49.5 (2C, U—CH₂), 31.9, 31.2, 30.7 (2C), 29.8, 29.7, (2C), 29.6 (2C), 29.5, 29.3, 26.2, 22.7, 21.7, 21.6 (CH₂—P, CH(CH₃)₂, P—O—CH₂—CH₂—CH₂—O, O—CH₂—CH₂—(CH₂)₁₃—CH₃), 14.1 (O—CH₂—CH₂—(CH₂)₁₃—CH₃).

³¹P NMR (162 MHz, CDCl₃): δ=26.5

EXAMPLE 32

N¹-[(E)-O-hexadecyloxypropyl isopropyloxycarbonyloxymethyl-phosphinyl-2-butenyl]thymin

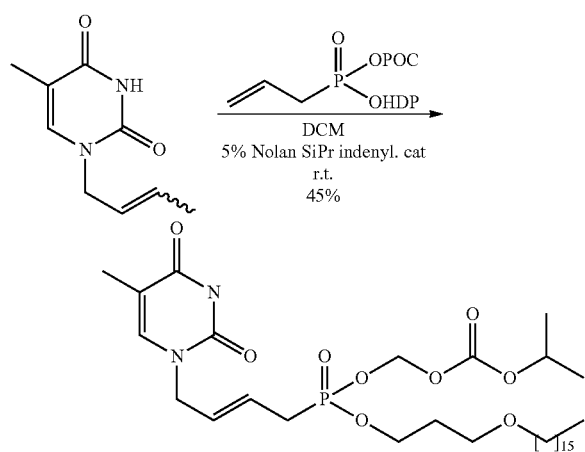

¹H NMR (400 MHz, CDCl₃): δ=9.08 (s, 1H, NH), 7.02 (d, J=3.9 Hz, 1H, H⁶), 5.73-5.48 (m, 4H, CH=CH, O—CH₂—O), 4.92 (sept., J=6.3 Hz, 2H, CH(CH₃)₂), 4.52 (t, J=4.4 Hz, 2H, U—CH₂), 4.22-4.08 (m, 2H, P—O—CH₂—CH₂—CH₂—O), 3.47 (t, J=6.2 Hz, 2H, P—O—CH₂—CH₂—CH₂—O), 3.39 (t, J=6.7 Hz, 2H, O—CH₂—CH₂—(CH₂)₁₃—CH₃), 2.64 (dd, J=22.2, 5.9 Hz, 2H, CH₂—P), 1.91 (m, 5H, P—O—CH₂—CH₂—CH₂—O, CH₃—U), 1.53 (p, J=6.9 Hz, 2H, O—CH₂—CH₂—(CH₂)₁₃—CH₃), 1.34-1.24 (m, 32H, O—CH₂—CH₂—(CH₂)₁₃—CH₃, CH(CH₃)₂), 0.88 (t, J=6.8 Hz, 3H, O—CH₂—CH₂—(CH₂)₁₃—CH₃).

¹³C NMR (100 MHz, CDCl₃): δ=163.6 (C=O), 153.2 (C=O), 152.2 (C=O), 134.3 (C⁶), 129.6 (2C, CH=CH), 122.6, 122.5 (CH=CH), 110.0 (C⁵), 84.5 (2C, O—CH₂—O), 77.2 (C⁵), 73.1 (CH(CH₃)₂), 71.2 (O—CH₂—CH₂—(CH₂)₁₃—CH₃), 66.5 (P—O—CH₂—CH₂—CH₂—O), 63.5, 63.4 (P—O—CH₂—CH₂—CH₂—O), 41.8 (2C, U—CH₂), 31.9, 31.3, 30.8, 30.7, 29.9, 29.7 (2C), 29.6 (2C), 29.5, 29.4, 26.2, 22.7, 21.7 (CH₂—P, CH(CH₃)₂, P—O—CH₂—CH₂—CH₂—O, O—CH₂—CH₂—(CH₂)₁₃—CH₃), 14.1 (O—CH₂—CH₂—(CH₂)₁₃—CH₃), 12.9 (CH₃—U).

³¹P NMR (162 MHz, CDCl₃): δ=26.6

EXAMPLE 33

N¹-[(E)-O-hexadecyloxypropyl isopropyloxycarbonyloxymethyl-phosphinyl-2-butenyl]-5-fluorouracil

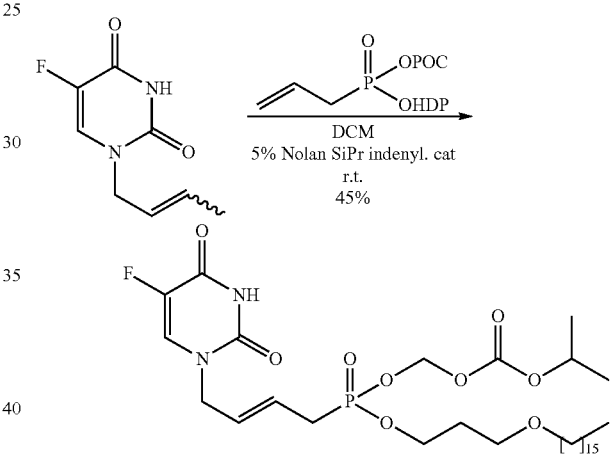

¹H NMR (400 MHz, CDCl₃): δ=8.67 (d, J=3.6 Hz, 1H, NH), 7.29 (d, J=5.5 Hz, 1H, H⁶), 5.82-5.59 (m, 4H CH=CH, O—CH₂—O), 4.93 (sept., J=6.3 Hz, 2H, CH(CH₃)₂), 4.38-4.26 (m, 2H, U—CH₂), 4.25-4.11 (m, 2H, P—O—CH₂—CH₂—CH₂—O), 3.47 (t, J=6.10 Hz, 2H, P—O—CH₂—CH₂—CH₂—O), 3.38 (t, J=6.7 Hz, 2H, O—CH₂—CH₂—(CH₂)₁₃—CH₃), 2.72 (dd, J=22.4, 6.6 Hz, 2H, CH₂—P), 1.92 (p, J=6.3 Hz, 2H, P—O—CH₂—CH₂—CH₂—O), 1.53 (p, J=6.7 Hz, 2H, O—CH₂—CH₂—(CH₂)₁₃—CH₃), 1.35-1.19 (m, 32H, O—CH₂—CH₂—(CH₂)₁₃—CH₃, CH(CH₃)₂), 0.88 (t, J=6.8 Hz, 3H, O—CH₂—CH₂—(CH₂)₁₃—CH₃).

¹³C NMR (100 MHz, CDCl₃): δ=156.9, 156.6 (C=O), 153.2 (C=O), 149.0 (C=O), 141.7, 139.3 (C⁶), 128.6, 128.4 (CH=CH), 127.7, 127.4 (C⁶), 125.7, 125.6 (CH=CH), 84.5, 84.4 (O—CH₂—O), 73.3 (CH(CH₃)₂), 71.2 (O—CH₂—CH₂—(CH₂)₁₃—CH₃), 66.4 (P—O—CH₂—CH₂—CH₂—O), 63.7, 63.6 (P—O—CH₂—CH₂—CH₂—O), 49.4, 49.3 (U—CH₂), 31.9 (2C), 31.2, 30.7 (2C), 29.8, 29.7, 29.6 (2C), 29.5 (2C), 29.3 (2C), 26.2, 22.7, 21.6 (2C)(CH₂—P, CH(CH₃)₂, P—O—CH₂—CH₂—CH₂—O, O—CH₂—CH₂—(CH₂)₁₃—CH₃) 14.1 (O—CH₂—CH₂—(CH₂)₁₃—CH₃).

³¹P NMR (162 MHz, CDCl₃): δ=26.5

EXAMPLE 34

N$^1$-[(E)-4-hexadecylpropyl-phosphinyl-2-butenyl] uracil

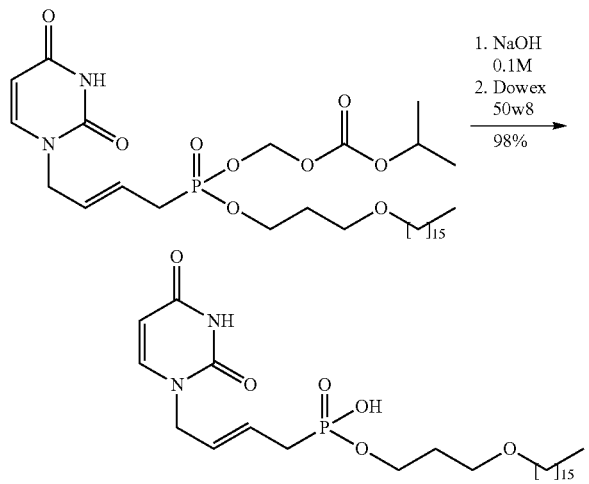

$^1$H NMR (400 MHz, CD$_3$OD): δ=7.54 (d, 1H, J=7.9 Hz, H$^6$), 5.78-5.72 (m, 2H, CH=CH), 5.66 (dd, J=7.8, 1.9 Hz, 1H, H$^5$), 4.35 (t, J=4.1 Hz, 2H, U—CH$_2$), 4.07 (q, J=6.5 Hz, 2H, P—O—CH$_2$—CH$_2$—CH$_2$—O), 3.51 (t, J=6.2 Hz, 2H, P—O—CH$_2$—CH$_2$—CH$_2$—O), 3.42 (t, J=6.6 Hz, 2H, O—CH$_2$—CH$_2$—(CH$_2$)$_{13}$—CH$_3$), 2.64 (dd, J=22.0, 5.3 Hz, 2H, CH$_2$—P), 1.88 (p, J=6.24 Hz, 2H, P—O—CH$_2$—CH$_2$—CH$_2$—O), 1.56 (p, J=6.9 Hz, 2H, O—CH$_2$—CH$_2$—(CH$_2$)$_{13}$—CH$_3$), 1.38-1.25 (m, 26H, O—CH$_2$—CH$_2$—(CH$_2$)$_{13}$—CH$_3$), 0.90 (t, J=6.9 Hz, 3H, O—CH$_2$—CH$_2$—(CH$_2$)$_{13}$—CH$_3$).

$^{13}$C NMR (100 MHz, CDCl$_3$): δ=166.7 (C=O), 152.7 (C=O), 146.7 (C$^6$), 129.9, 129.8 (CH=CH), 126.6, 126.5 (CH=CH), 102.5 (C$^5$), 72.2 (O—CH$_2$—CH$_2$—(CH$_2$)$_{13}$—CH$_3$), 67.8 (P—O—CH$_2$—CH$_2$—CH$_2$—O), 64.0, 63.9 (P—O—CH$_2$—CH$_2$—CH$_2$—O), 50.3 (2C, U—CH$_2$), 33.1, 32.0, 30.8 (2C), 30.7, 30.5, 27.3, 23.8 (CH$_2$—P, P—O—CH$_2$—CH$_2$—CH$_2$—O, O—CH$_2$—CH$_2$—(CH$_2$)$_{13}$—CH$_3$), 14.5 (O—CH$_2$—CH$_2$—(CH$_2$)$_{13}$—CH$_3$).

$^{31}$P NMR (162 MHz, CDCl$_3$): δ=25.9.

EXAMPLE 35

N$^1$-[(E)-O-hexadecyloxypropyl-phosphinyl-2-butenyl]-5-chlorouracil

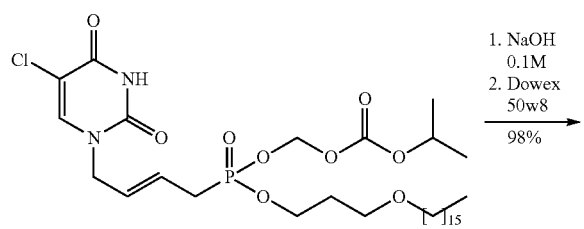

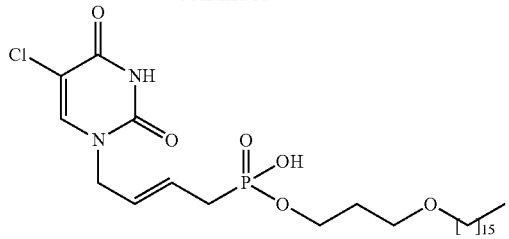

$^1$H NMR (400 MHz, CD$_3$OD): δ=7.89 (s, 1H, H$^6$), 5.85-5.68 (m, 2H, CH=CH), 4.35 (t, J=4.2 Hz, 2H, U—CH$_2$), 4.07 (q, J=6.5 Hz, 2H, P—O—CH$_2$—CH$_2$—CH$_2$—O), 3.51 (t, J=6.2 Hz, 2H, P—O—CH$_2$—CH$_2$—CH$_2$—O), 3.42 (t, J=6.6 Hz, 2H, O—CH$_2$—CH$_2$—(CH$_2$)$_{13}$—CH$_3$), 2.64 (dd, J=21.6, 5.9 Hz, 2H, CH$_2$—P), 1.89 (p, J=6.2 Hz, 2H, P—O—CH$_2$—CH$_2$—CH$_2$—O), 1.56 (p, 1H, J=6.9 Hz, 2H, O—CH$_2$—CH$_2$—(CH$_2$)$_{13}$—CH$_3$), 1.39-1.25 (m, 26H, O—CH$_2$—CH$_2$—(CH$_2$)$_{13}$—CH$_3$), 0.90 (t, J=6.9 Hz, 3H, O—CH$_2$—CH$_2$—(CH$_2$)$_{13}$—CH$_3$).

$^{13}$C NMR (100 MHz, CD$_3$OD): δ=161.9 (C=O), 151.8 (C=O), 143.6 (C$^6$), 129.6, 129.4 (CH=CH), 127.2, 127.1 (CH=CH), 109.0 (C$^5$), 72.2 (O—CH$_2$—CH$_2$—(CH$_2$)$_{13}$—CH$_3$), 67.8 (P—O—CH$_2$—CH$_2$—CH$_2$—O), 63.9 (2C, P—O—CH$_2$—CH$_2$—CH$_2$—O), 50.6 (2C, U—CH$_2$), 33.1, 32.1, 32.0, 30.8 (2C), 30.7, 30.5, 27.3, 23.8 (CH$_2$—P, P—O—CH$_2$—CH$_2$—CH$_2$—O, O—CH$_2$—CH$_2$—(CH$_2$)$_{13}$—CH$_3$), 14.5 (O—CH$_2$—CH$_2$—(CH$_2$)$_{13}$—CH$_3$).

$^{31}$P NMR (162 MHz, CD$_3$OD): δ=25.4.

EXAMPLE 36

N$^1$-[(E)-O-hexadecyloxypropyl-phosphinyl-2-butenyl]-5-bromorouracil

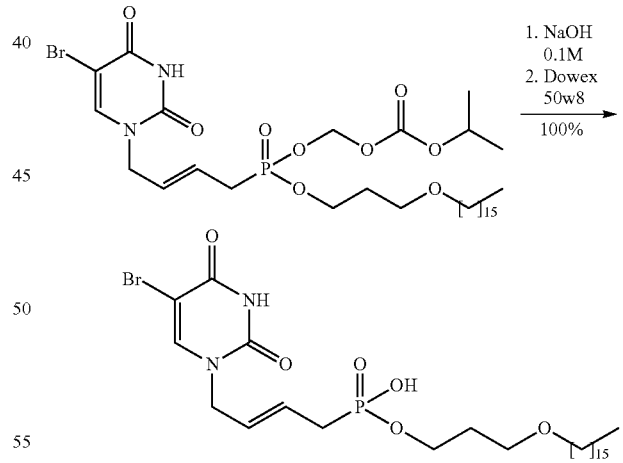

$^1$H NMR (400 MHz, CD$_3$OD): δ=7.98 (s, 1H, H$^6$), 5.83-5.70 (m, 2H, CH=CH), 4.36 (t, J=3.9 Hz, 2H, U—CH$_2$), 4.08 (q, J=6.5 Hz, 2H, P—O—CH$_2$—CH$_2$—CH$_2$—O), 3.51 (t, J=6.1 Hz, 2H, P—O—CH$_2$—CH$_2$—CH$_2$—O), 3.42 (t, J=6.6 Hz, 2H, O—CH$_2$—CH$_2$—(CH$_2$)$_{13}$—CH$_3$), 2.65 (dd, J=21.6, 5.4 Hz, 2H, CH$_2$—P), 1.89 (p, J=6.3 Hz, 2H, P—O—CH$_2$—CH$_2$—CH$_2$—O), 1.55 (p, 2H, J=6.9 Hz, 2H, O—CH$_2$—CH$_2$—(CH$_2$)$_{13}$—CH$_3$), 1.40-1.23 (m, 26H, O—CH$_2$—CH$_2$—(CH$_2$)$_{13}$—CH$_3$), 0.90 (t, J=6.8 Hz, 3H, O—CH$_2$—CH$_2$—(CH$_2$)$_{13}$—CH$_3$).

$^{13}$C NMR (100 MHz, CD$_3$OD): δ=152.1 (C=O), 146.2 (C=O, C$^6$), 129.8, 129.6 (CH=CH), 127.0, 126.9 (CH=CH), 96.7 (C$^5$), 72.2 (O—CH$_2$—CH$_2$—(CH$_2$)$_{13}$—CH$_3$), 67.7 (P—O—CH$_2$—CH$_2$—CH$_2$—O), 64.0 (2C, P—O—CH$_2$—CH$_2$—CH$_2$—O), 50.6 (2C, U—CH$_2$), 33.1, 32.0 2C), 31.9, 30.8 (2C), 30.7, 30.5, 27.4, 23.8 (CH$_2$—P, P—O—CH$_2$—CH$_2$—CH$_2$—O, O—CH$_2$—CH$_2$—(CH$_2$)$_{13}$—CH$_3$), 14.5 (O—CH$_2$—CH$_2$—(CH$_2$)$_{13}$—CH$_3$).

$^{31}$P NMR (162 MHz, CD$_3$OD): δ=25.7.

EXAMPLE 37

N$^1$-[(E)-O-hexadecyloxypropyl-phosphinyl-2-butenyl]-5-fluorouracil

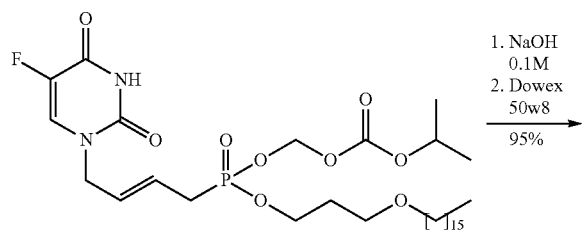

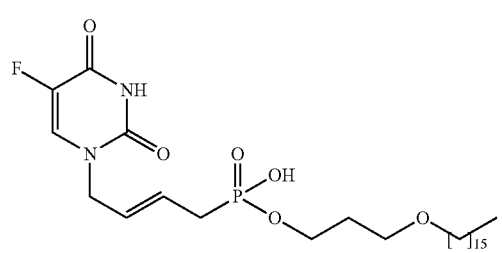

$^1$H NMR (400 MHz, CD$_3$OD): δ=7.78 (d, J=6.2 Hz, 1H, H$^6$), 5.83-5.69 (m, 1H, CH=CH)), 4.31 (t, J=4.2 Hz, 2H, U—CH$_2$), 4.07 (q, J=6.4 Hz, 2H, P—O—CH$_2$—CH$_2$—O), 3.51 (t, J=6.2 Hz, 2H, P—O—CH$_2$—CH$_2$—CH$_2$—O), 3.42 (t, J=6.6 Hz, 2H, O—CH$_2$—CH$_2$—(CH$_2$)$_{13}$—CH$_3$), 2.64 (dd, J=21.6, 6.0 Hz, 2H, CH$_2$—P), 1.89 (p, J=6.3 Hz, 2H, P—O—CH$_2$—CH$_2$—CH$_2$—O), 1.55 (p, J=6.7 Hz, 2H, O—CH$_2$—CH$_2$—(CH$_2$)$_{13}$—CH$_3$), 1.35-1.25 (m, 26H, O—CH$_2$—CH$_2$—(CH$_2$)$_{13}$—CH$_3$), 0.90 (t, J=6.8 Hz, 3H, O—CH$_2$—CH$_2$—(CH$_2$)$_{13}$—CH$_3$).

$^{13}$C NMR (100 MHz, CD$_3$OD): δ=159.9, 159.7 (C=O), 151.3 (C=O), 142.9, 140.6 (C$^5$), 130.7, 130.4 (C$^6$), 129.5, 129.4 (CH=CH), 127.2, 127.1 (CH=CH), 72.2 (O—CH$_2$—CH$_2$—(CH$_2$)$_{13}$—CH$_3$), 67.8 (P—O—CH$_2$—CH$_2$—CH$_2$—O), 63.9, 63.8 (P—O—CH$_2$—CH$_2$—CH$_2$—O), 50.4 (2C, U—CH$_2$), 33.1, 32.0 (3C), 30.8 (2C), 30.7, 30.5, 27.3, 23.8 (CH$_2$—P, P—O—CH$_2$—CH$_2$—CH$_2$—O, O—CH$_2$—CH$_2$—(CH$_2$)$_{13}$—CH$_3$), 14.5 (O—CH$_2$—CH$_2$—(CH$_2$)$_{13}$—CH$_3$).

$^{31}$P NMR (162 MHz, CD$_3$OD): δ=25.4.

EXAMPLE 38

N$^1$-[(E)-O-hexadecyloxypropyl-phosphinyl-2-butenyl]thymin

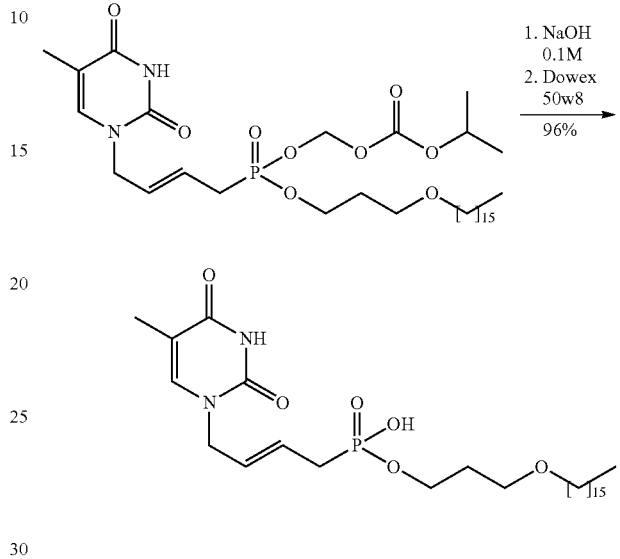

$^1$H NMR (400 MHz, CD$_3$OD): δ=7.22 (d, J=1.1 Hz, 1H, H$^6$), 5.78-5.64 (m, 2H, CH=CH), 4.50 (m, 2H, U—CH$_2$), 4.05 (m, 2H, P—O—CH$_2$—CH$_2$—CH$_2$—O), 3.50 (t, J=6.1 Hz, 2H, P—O—CH$_2$—CH$_2$—CH$_2$—O), 3.43 (dt, J=6.5 Hz, 2H, O—CH$_2$—CH$_2$—(CH$_2$)$_{13}$—CH$_3$), 2.59 (d, J=18.4 Hz, 2H), 1.94-1.83 (m, 5H, P—O—CH$_2$—CH$_2$—CH$_2$—O, CH$_3$—U)), 1.60-1.51 (p, 2H, J=6.9 Hz, 2H, O—CH$_2$—CH$_2$—(CH$_2$)$_{13}$—CH$_3$), 1.37-1.24 (m, 26H, O—CH$_2$—CH$_2$—(CH$_2$)$_{13}$—CH$_3$), 0.90 (t, J=6.9 Hz, 3H, CH$_3$—U).

$^{13}$C NMR (100 MHz, CD$_3$OD): δ=166.0 (C=O), 153.2 (C=O), 137.5 (C$^6$), 110.0 (C$^5$), 72.2 (O—CH$_2$—CH$_2$—(CH$_2$)$_{13}$—CH$_3$), 67.8 (P—O—CH$_2$—CH$_2$—CH$_2$—O), 64.0, 63.9 (P—O—CH$_2$—CH$_2$—CH$_2$—O), 42.8 (2C, U—CH$_2$), 33.1, 32.0 (2C), 30.8, 30.7 (2C), 30.5, 27.3, 23.8 (CH$_2$—P, P—O—CH$_2$—CH$_2$—CH$_2$—O, O—CH$_2$—CH$_2$—(CH$_2$)$_{13}$—CH$_3$), 15.9, 14.5 (O—CH$_2$—CH$_2$—(CH$_2$)$_{13}$—CH$_3$), 12.9 (CH$_3$—U).

EXAMPLE 39

General Procedure for Mitsunobu Reaction with Heterocyclic Bases

To a dioxane (5 mL/mmol) solution of Bis-(POM) 1-hydroxymethyl-allylphosphonate (1 eq.) prepared according to example 13, heterocyclic base (1.5 eq.), triphenylphosphine (1.5 eq.) was added diisopropylazodicarboxylate (1.5 eq). under argon at 10° C. This solution was stirred a room temperature for 20 h. After evaporation of all volatiles, the residue was purified by chromatography on silica gel (MeOH/DCM).

The compounds of examples 40 to 42 are synthesized according to said general procedure.

EXAMPLE 40

N$^9$-[(E)-4-bispivaloyloxymethylphosphinyl-2-butenyl]adenine

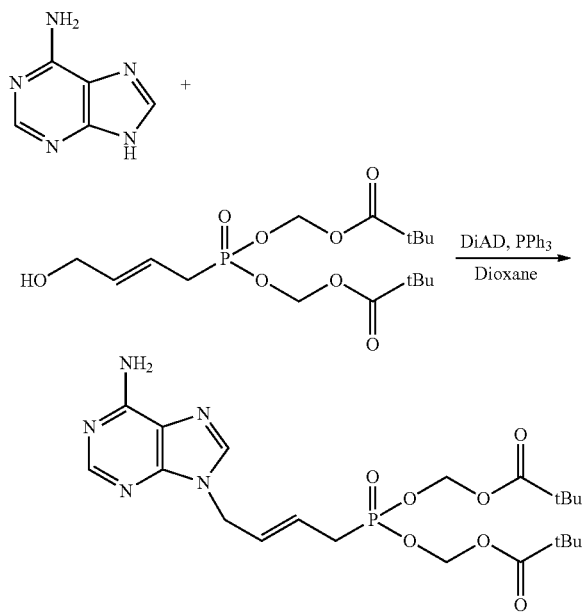

<sup>1</sup>H NMR (400 MHz, CDCl$_3$): δ=8.36 (s, 1H, H$_2$), 7.81 (s, 1H, H$_8$), 5.95-5.85 (m, 1H, CH=CH), 5.74-5.60 (m, 7H, CH=CH, O—CH$_2$—O, NH$_2$), 4.80 (t, J=5.0 Hz, 2H, B—CH$_2$), 2.72 (dd, J=22.6, 7.3 Hz, 2H, CH$_2$—P), 1.23 (s, 18H, C(CH$_3$)$_3$).

<sup>13</sup>C NMR (100 MHz, CDCl$_3$): δ=176.8 (C=O), 155.4 (C$_6$), 153.1 (C$_2$), 149.9 (C$_4$), 140.1 (C$_8$), 130.0, 129.8 (CH=CH), 123.4, 123.2 (CH=CH), 119.6 (C$_5$), 81.6 (2C, O—CH$_2$—O), 44.9 (2C, B—CH$_2$), 38.7 (C(CH$_3$)$_3$), 31.5, 30.1 (CH$_2$—P), 26.8 (C(CH$_3$)$_3$).

<sup>31</sup>P NMR (162 MHz, CDCl$_3$): δ=26.50

EXAMPLE 41

N$^9$-[(E)-4-bispivaloyloxymethylphosphinyl-2-butenyl]-6-chloropurine

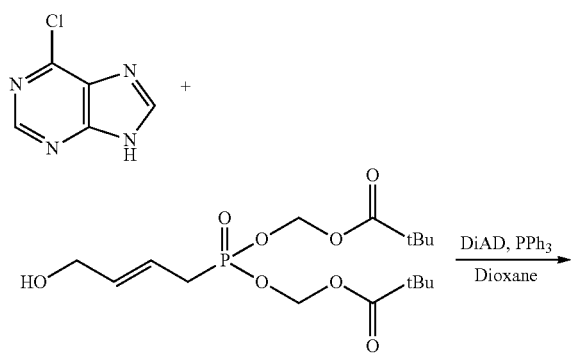

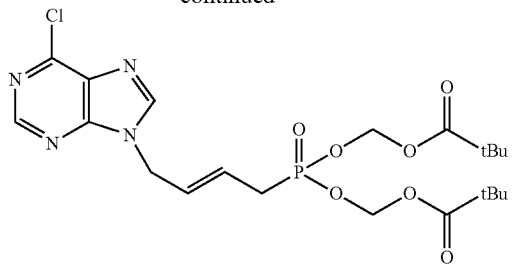

<sup>1</sup>H NMR (400 MHz, CDCl$_3$): δ=8.73 (s, 1H, H$_2$), 8.14 (s, 1H, H$_8$), 5.94-5.85 (m, 1H, CH=CH), 5.80-5.71 (m, 1H, CH=CH), 5.71-5.67 (m, 4H, O—CH$_2$—O), 4.88 (t, J=5.2 Hz, 2H, B—CH$_2$), 2.71 (dd, J=22.8, 7.1 Hz, 2H, CH$_2$—P), 1.21 (s, 18H, C(CH$_3$)$_3$).

<sup>13</sup>C NMR (100 MHz, CDCl$_3$): δ=176.8 (C=O), 152.0 (C$_2$), 151.6, 151.1 (C$_4$ and C$_6$), 144.7 (C$_8$), 131.6 (C$_5$), 128.9, 128.7 (CH=CH), 124.6, 124.5 (CH=CH), 81.6, 81.5 (O—CH$_2$—O), 45.5, 45.4 (B—CH$_2$), 38.7 (C(CH$_3$)$_3$), 31.4, 30.0 (CH$_2$—P), 26.8 (C(CH$_3$)$_3$).

<sup>31</sup>P NMR (162 MHz, CDCl$_3$): δ=26.05.

EXAMPLE 42

N$^9$-[(E)-4-bispivaloyloxymethylphosphinyl-2-butenyl]-2-Amino-6-chloropurine

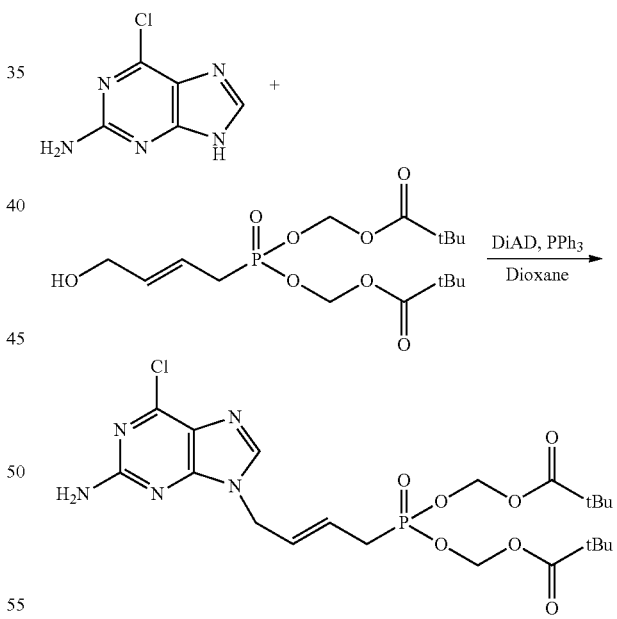

<sup>1</sup>H NMR (400 MHz, CDCl$_3$): δ=7.74 (s, 1H, H$_2$), 5.88-5.79 (m, 1H, CH=CH), 5.72-5.59 (m, 5H, CH=CH, O—CH$_2$—O), 5.28 (s, 2H, NH$_2$), 4.65 (t, J=5.1 Hz, 2H, B—CH$_2$), 2.70 (dd, J=22.7, 7.2 Hz, 2H, CH$_2$—P), 1.20 (s, 18H, C(CH$_3$)$_3$).

<sup>13</sup>C NMR (162 MHz, CDCl$_3$): δ=176.8 (C=O), 159.1 (C$_6$), 153.6 (C$_4$), 151.3 (C$_2$), 141.8 (C$_8$), 129.4, 129.3 (CH=CH), 125.1 (C$_5$), 123.6, 123.5 (CH=CH), 81.6, 81.5 (O—CH$_2$—O), 44.9 (B—CH$_2$), 38.7 (C(CH$_3$)$_3$), 31.4, 30.0 (CH$_2$—P), 26.8 (C(CH$_3$)$_3$).

<sup>31</sup>P NMR (162 MHz, CDCl$_3$): δ=26.35.

EXAMPLE 43

General Procedure for Conversion of 6-Chloropurines to 6-Cyclopropylamino Purines A solution of 6-chloropurine in 1:9 mixture of cyclopropylamine and dichloromethane (20 mL/mmol) is stirred for 20 h at 40° C. After evaporation of all volatiles, the residue was purified by chromatography on silica gel (MeOH/DCM).

The compounds of examples 44 and 45 are prepared according this procedure.

EXAMPLE 44

$N^9$-[(E)-4-bispivaloyloxymethylphosphinyl-2-butenyl]-6-cyclopropylaminopurine

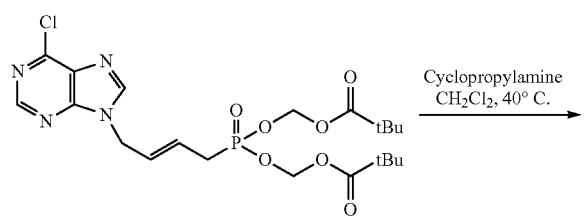

$^1$H NMR (400 MHz, CDCl$_3$): δ=8.47 (s, 1H, H$_2$), 7.75 (s, 1H, H$_8$), 5.95 (s, 1H, NH), 5.93-5.84 (m, 1H, CH=CH), 5.69-5.61 (m, 5H, CH=CH, O—CH$_2$—O), 4.78 (t, J=5.1 Hz, 2H, B—CH$_2$), 3.04 (d, J=3.0 Hz, 1H, NHCH), 2.70 (dd, J=22.6, 7.3 Hz, 2H, CH$_2$—P), 1.21 (s, 18H, C(CH$_3$)$_3$), 0.94 (td, J=8.4 Hz, 6.9 Hz, 2H, NHCHCH$_2$), 0.68-0.64 (m, 2H, NHCHCH$_2$).

$^{13}$C NMR (100 MHz, CDCl$_3$): δ=176.8 (C=O), 155.8 (C$_6$), 153.3 (C$_2$), 149.0 (C$_4$), 139.5 (C$_8$), 130.1, 129.9 (CH=CH), 123.2, 123.0 (CH=CH), 119.8 (C$_5$), 81.6, 81.5 (O—CH$_2$—O), 44.8 (2C, B—CH$_2$), 38.7 (C(CH$_3$)$_3$), 31.5, 30.1 (CH$_2$—P), 26.8 (C(CH$_3$)$_3$), 23.7 (NHCH), 7.4 (NHCHCH$_2$).

$^{31}$P NMR (162 MHz, CDCl$_3$): δ=26.57

EXAMPLE 45

$N^9$-[(E)-4-bispivaloyloxymethylphosphinyl-2-butenyl]-6-cyclopropylaminopurine

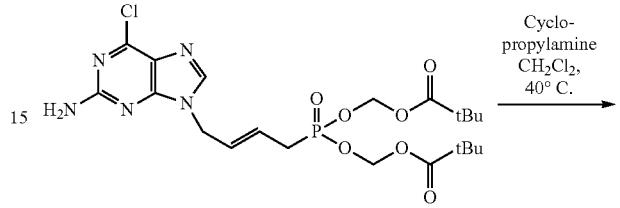

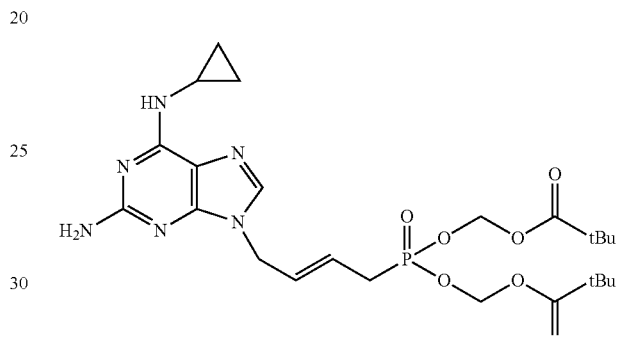

$^1$H NMR (400 MHz, CDCl$_3$): δ=7.44 (s, 1H, H$_2$), 5.89-5.81 (m, 1H, CH=CH), 5.76 (s, 1H, NH), 5.67-5.57 (m, 5H, CH=CH, O—CH$_2$—O), 4.79 (s, 2H, NH$_2$), 4.61 (t, J=5.1 Hz, 2H, B—CH$_2$), 3.05-2.95 (m, 1H, NHCH), 2.69 (dd, J=23.0, 7.0 Hz, 2H, CH$_2$—P), 1.22 (s, 18H, C(CH$_3$)$_3$), 0.85 (td, J=6.9, 5.4 Hz, 2H, NHCHCH$_2$), 0.63-0.58 (m, 2H, NHCHCH$_2$).

$^{13}$C NMR (100 MHz, CDCl$_3$): δ=176.8 (C=O), 160.1, 156.3 (C$_6$ and C$_2$), 151.0 (C$_4$), 136.9 (C$_8$), 130.6, 130.4 (CH=CH), 122.4, 122.3 (CH=CH), 114.6 (C$_5$), 81.6 (2C, O—CH$_2$—O), 44.4, 44.3 (2C, B—CH$_2$), 38.7 (C(CH$_3$)$_3$), 31.4, 30.0 (CH$_2$—P), 26.8 (C(CH$_3$)$_3$), 23.7 (NHCH), 7.4 (NHCHCH$_2$).

$^{31}$P NMR (162 MHz, CDCl$_3$): δ=26.77.

EXAMPLE 46

General Procedure for Conversion 6-Chloropurines to 6-Hydroxy Purines

A solution of 6-chloropurine in 1:1 mixture of demineralized water and formic acid (20 mL/mmol) is stirred for 20 h at 40° C. After evaporation of all volatiles, the residue was purified by chromatography on silica gel (MeOH/DCM).

Compounds of examples 47 and 48 are synthesized according to this procedure.

EXAMPLE 47

N⁹-[(E)-4-bispivaloyloxymethylphosphinyl-2-butenyl]hypoxanthine

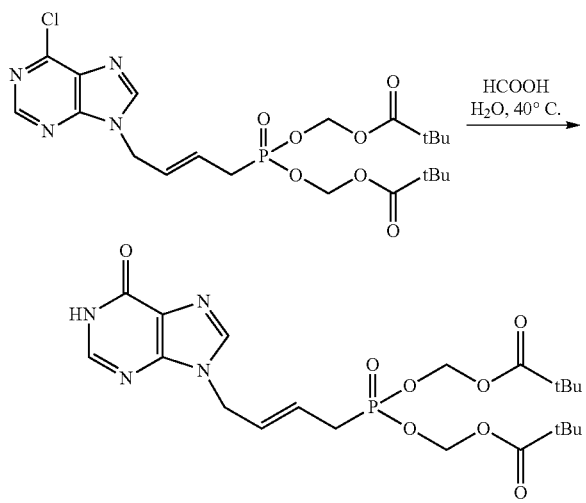

¹H NMR (400 MHz, CDCl₃): δ=12.94 (s, 1H, NH), 8.17 (s, 1H, H₂), 7.81 (s, 1H, H₈), 5.94-5.83 (m, 1H, CH=CH), 5.78-5.60 (m, 5H, CH=CH, O—CH₂—O), 4.78 (t, J=5.2 Hz, 2H, B—CH₂), 2.72 (dd, J=22.7, 7.2 Hz, 2H), 1.21 (s, 18H, C(CH₃)₃).
¹³C NMR (100 MHz, CDCl₃): δ=176.8 (C=O), 159.1 (C₆), 148.9 (C₄), 145.0 (C₂), 139.7 (C₈), 129.7, 129.5 (CH=CH), 124.5 (C₅), 123.8, 123.7 (CH=CH), 81.6 (2C, O—CH₂—O), 45.3 (2C, B—CH₂), 38.7 (C(CH₃)₃), 31.4, 30.0 (CH₂—P), 26.8 (C(CH₃)₃).
³¹P NMR (162 MHz, CDCl₃): δ=26.40.

EXAMPLE 48

N⁹-[(E)-4-bispivaloyloxymethylphosphinyl-2-butenyl]guanine

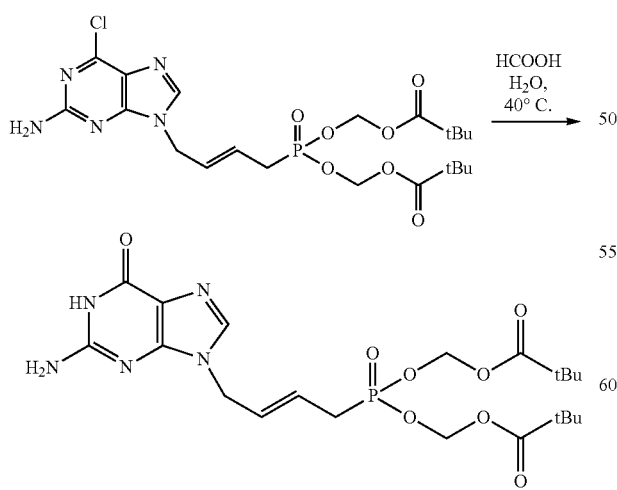

¹H NMR (400 MHz, CDCl₃): δ=12.11 (s, 1H, NH), 7.60 (s, 1H, H₈), 6.65 (s, 2H, NH₂), 5.95-5.84 (m, 1H, CH=CH), 5.73-5.62 (m, 5H, CH=CH, O—CH₂—O), 4.60 (t, J=4.7 Hz, 2H, B—CH₂), 2.72 (dd, J=22.6, 7.3 Hz, 2H), 1.20 (s, 18H, C(CH₃)₃).
¹³C NMR (100 MHz, CDCl₃): δ=176.9 (C=O), 159.0 (C₆), 153.9 (C₂), 151.4 (C₄), 137.2 (C₈), 130.6, 130.4 (CH=CH), 122.7, 122.6 (CH=CH), 116.8 (C₅), 81.7, 81.6 (O—CH₂—O), 44.8 (B—CH₂), 38.7 (C(CH₃)₃), 31.4, 30.0 (CH₂—P), 26.8 (C(CH₃)₃).
³¹P NMR (100 MHz, CDCl₃): δ=27.04.

EXAMPLE 49

Bioavailability of the Compounds According to the Invention

Log D (pH=7.4) was calculated using MarvinSketch 5.3 (Method Weighter) from ChemAxon.
Results are given in FIG. 1 which presents the Log D i.e. the logarithm of the water/octanol partition ratio at pH=7.4.
The greater is the Log D, the more the compound will be lipophilic and so the better will be its bioavailability.
The compounds according to the invention (examples 16 to 48) with the claimed formula R=R'=POM; R=R'=POC; R=POC and R'=HDP, and R=H and R'=HDP) all have a much greater Log D than the corresponding phosphoric acid (R=R'=H).

The invention claimed is:
1. A compound of formula (I)

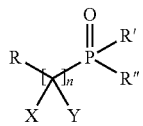

wherein
R represents
a group of formula (1)

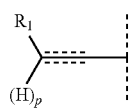

wherein R₁ represents H, a straight or branched (C₁-C₆) alkyl group or a —(CH₂)ₘ—R₂ group with R₂ selected from the group consisting of hydrogen, halogen, OH, N₃, NH₂, epoxy groups, leaving groups and carbonyl groups and m is an integer from 0 to 5,
═══ represents a double or a triple bond,
p being equal to ═══ 0 when is a triple bond and equal to 1 when
═══ is a double bond or,
R=R₂ with R₂ selected from the group consisting of hydrogen, halogen, OH, N₃, NH₂, epoxy groups and analogs, leaving groups, leaving groups involved into a transmetalation step catalyzed by Pd(0), and carbonyl groups,
n is an integer from 0 to 5
X and Y independently of each other represent hydrogen, halogen or a straight or branched (C₁-C₆)alkyl group or an hydroxymethyl group, and R' and R" independently of each other represent a group selected from the group consisting of an oxymethylcarbonyl group of formula (2)

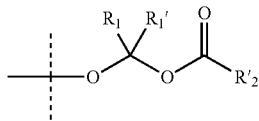
(2)

wherein
R$_1$ and R'$_1$ are independently of each other hydrogen or (C$_1$-C$_4$)alkyl group and
R'$_2$ is a straight or branched (C$_1$-C$_6$)alkyl group or straight or branched (C$_1$-C$_6$)alkoxy group
with the proviso that when R is cis-propenyl

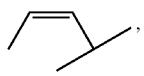

n=0 and R'2 is methyl, then R1 and R'1 are not simultaneously hydrogen,
a thioethylcarbonyl group of formula (3)

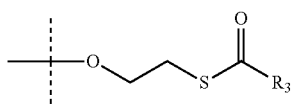
(3)

wherein
R$_3$ is a straight or branched (C$_1$-C$_6$) alkyl group
a lipohilic chain selected from the group consisting of hexadecyloxypropyl (HDP)-, octadecyloxyethyl-, oleyloxypropyl-, and oleyloxyethyl-esters with the proviso that when n=0 then R is not the cis-propenyl

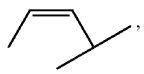

or
R' and R" form with the phosphate atom to which they are linked a cycloalkyle group of formula (4)

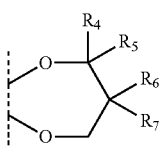
(4)

wherein R$_4$, R$_5$, R$_6$, and R$_7$ each independently represent a straight or branched (C$_1$-C$_6$)alkyl or aryl group or R$_4$ and R$_7$ independently represent a straight or branched (C$_1$-C$_6$) alkyl or aryl group or R$_5$ and R$_6$ form together an aromatic ring, said aromatic ring being optionally substituted with the proviso that

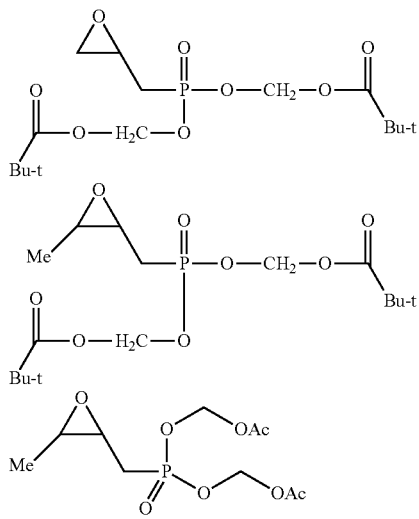

are excluded.

2. The compound according to claim 1, corresponding to formula

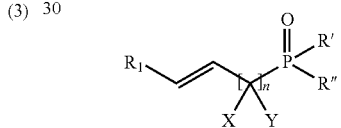
(I-1)

wherein

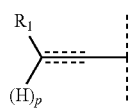

is a group

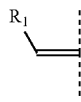

with R$_1$ as defined above.

3. The compound according to claim 1, corresponding to formula

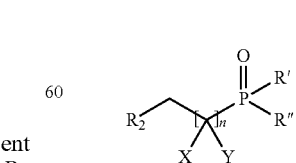
(I-2)

wherein R is equal to R$_2$ as defined above.

4. The compound according to claim 1, wherein the compound is selected from the group consisting of:

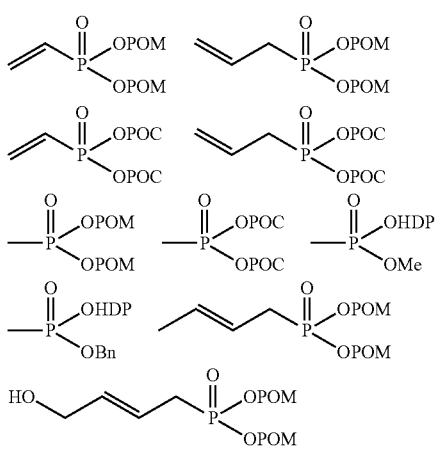
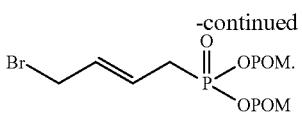
5. The compound of claim 1, wherein the compound is selected from the group consisting of:
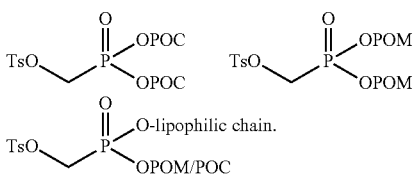
* * * * *